(12) United States Patent
Hargis et al.

(10) Patent No.: US 10,959,447 B2
(45) Date of Patent: Mar. 30, 2021

(54) COMPOSITIONS, PROBIOTIC FORMULATIONS AND METHODS TO PROMOTE DIGESTION AND IMPROVE NUTRITION IN POULTRY

(71) Applicant: THE BOARD OF TRUSTEES OF THE UNIVERSITY OF ARKANSAS, Little Rock, AR (US)

(72) Inventors: Billy Hargis, Fayetteville, AR (US); Guillermo Tellez, Fayetteville, AR (US); Juan David Latorre, Fayetteville, AR (US); Ross Wolfenden, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 22 days.

(21) Appl. No.: 15/744,932

(22) PCT Filed: Jul. 13, 2016

(86) PCT No.: PCT/US2016/041977
§ 371 (c)(1),
(2) Date: Jan. 15, 2018

(87) PCT Pub. No.: WO2017/011489
PCT Pub. Date: Jan. 19, 2017

(65) Prior Publication Data
US 2018/0206525 A1 Jul. 26, 2018

Related U.S. Application Data

(60) Provisional application No. 62/192,501, filed on Jul. 14, 2015.

(51) Int. Cl.
*A23K 10/18* (2016.01)
*A23K 20/189* (2016.01)
(Continued)

(52) U.S. Cl.
CPC ............ *A23K 10/18* (2016.05); *A23K 20/189* (2016.05); *A23K 50/75* (2016.05); *A61K 9/0056* (2013.01);
(Continued)

(58) Field of Classification Search
CPC ........ A01N 25/00; A01N 37/44; A01N 63/00; A01N 63/02; A01N 37/46; A01N 43/16; A01N 59/00; A01N 63/04; A01N 2300/00; A23K 10/18; A23K 50/75; A23K 20/163; A23K 50/10; A23K 10/30; A23K 20/10; A23K 20/158; A23K 50/80; A23K 40/35; A23K 10/37; A23K 20/28; A23K 50/30; A23K 50/90; A23K 20/147; A23K 20/189; A23K 40/10; A23K 50/20; A23K 10/12; A23K 40/30; A23K 20/142; A23K 20/174; A23K 20/30; A23K 40/00; A23K 10/16; A23K 30/00; A23K 50/00; A23K 50/40; A23K 50/60; C12N 1/20; C12N 1/14; C12N 15/62; C12N 15/75; C12N 3/00; C12N 1/12; C12N 1/16; A61K 35/742; A61K 33/44; A61K 35/74; A61K 9/0053; A61K 9/1611; A61K 9/1682; A61K 35/741; A61K 2035/115; A61K 36/064; A61K 35/748; A61K 36/06; A61K 36/062; A61K 39/02; A61K 9/0019; A61K 9/0056; A61K 9/1652; A61K 31/4155; A61K 9/0014; A61K 35/747; A61K 39/00; A61K 47/12; A61K 47/02; A61K 9/167; A61K 9/5036; A61K 2035/11; A61K 35/66; A61K 35/744; A61K 38/47; A61L 9/012; A61L 9/014; A61L 2/18; A61L 2/07; A61L 2/22; C05B 17/00; C05C 5/00; C05D 9/00; C05G 3/04; C05G 3/0058; C09K 17/50; C09K 17/04; C09K 17/48; C09K 2208/24; C09K 8/582; C09K 8/62; C09K 17/00; B01J 20/12; B01J 20/20; B01J 20/24; B01J 20/28019; B01J 20/3007; B01J 20/3028; B01J 20/3042; B01J 20/3078; B01J 2/00; B01J 2/28; B01J 2/12; C02F 3/348; C02F 3/34;
(Continued)

(56) References Cited

U.S. PATENT DOCUMENTS 9,005,601 B2 * 4/2015 Hargis ................ A61K 35/742
424/93.46
2008/0050779 A1 * 2/2008 Defachelles ............ C12N 1/14
435/71.1
(Continued)

FOREIGN PATENT DOCUMENTS

WO 080200 * 9/2004

OTHER PUBLICATIONS

Adeola, O., et al. "Board-invited review: opportunities and challenges in using exogenous enzymes to improve nonruminant animal production." Journal of animal science 89.10 (2011): 3189-3218.
(Continued)

*Primary Examiner* — Deborah K Ware
(74) *Attorney, Agent, or Firm* — Quarles & Brady LLP

(57) ABSTRACT

The present disclosure relates to probiotic compositions, formulations and methods for promoting digestion and improving nutrition in birds, and probiotic compositions and formulations for increasing enzyme production and improving parameters and indications in birds.

17 Claims, 5 Drawing Sheets

(51) Int. Cl.
| | |
|---|---|
| A23K 50/75 | (2016.01) |
| C12R 1/07 | (2006.01) |
| C12R 1/10 | (2006.01) |
| A61K 9/00 | (2006.01) |
| A61K 35/742 | (2015.01) |
| C12Q 1/04 | (2006.01) |

(52) U.S. Cl.
CPC .............. *A61K 35/742* (2013.01); *C12Q 1/04* (2013.01); *C12R 1/07* (2013.01); *C12R 1/10* (2013.01)

(58) Field of Classification Search
CPC .. C02F 11/04; C02F 2101/10; C02F 2101/30; C02F 2103/002; C02F 2103/003; C02F 2103/007; C02F 2103/06; C02F 2103/10; C02F 2103/14; C02F 2103/16; C02F 2103/26; C02F 2103/28; C02F 3/342; C02F 3/341; C02F 3/347; A23L 31/10; A23L 33/135; A23L 2/52; A23L 33/10; A61P 15/04; A61P 31/04; A61P 1/04; C01B 32/05; A23V 2002/00; B65D 65/38; B65D 81/18; C05F 11/00; C05F 11/08; C05F 17/0045; C05F 11/02; C05F 17/009; C05F 9/04; C07D 409/12; Y02E 50/343; Y02W 30/47; Y02W 10/23; Y02W 30/43; Y02W 10/37; B09C 1/10; B09C 1/105; B09C 2101/00; C07K 14/32; C07K 2319/01; C07K 2319/035; C07K 2319/40; C11D 3/221; C11D 3/33; C11D 3/381; C12P 21/02; C12P 5/023; C12R 1/125; C12R 1/07; C12R 1/225; C12R 1/865; C12R 1/01; C12R 1/10; E21B 43/16; Y02A 40/818; Y02A 40/216; Y02P 20/145; C12Q 1/04; Y02C 10/08; A01K 45/00; A23Y 2220/00; C12Y 302/01008; C12Y 302/01021
See application file for complete search history.

(56) References Cited

U.S. PATENT DOCUMENTS

| | | | | |
|---|---|---|---|---|
| 2011/0021461 | A1* | 1/2011 | Vazquez-Anon | A61K 31/47 514/64 |
| 2017/0096657 | A1* | 4/2017 | Gosselin | C02F 3/107 |

OTHER PUBLICATIONS

Ahmed, S. T., et al. "Effects of Bacillus amyloliquefaciens as a probiotic strain on growth performance, cecal microflora, and fecal noxious gas emissions of broiler chickens." Poultry Science 93.8 (2014): 1963-1971.
Alvarez-Olmos, M.I., et al. (2001). Probiotic agents and infectious diseases: a modern perspective on a traditional therapy. C!in. Infect. Dis. 32, 1567-1576.
Annett, C.B., et al. (2002). Necrotic enteritis: effect of barley, wheat and corn diets on proliferation of C/ostridium perfringens type A. Avian Pa/ho/. 31, 598-601.
Barbosa, T. M., et al. "Screening for Bacillus isolates in the broiler gastrointestinal tract." Appl. Environ. Microbiol. 71.2 (2005): 968-978.
Bedford, M.R., et al. (1991). The effect of pelleting, salt, and pentosanase on the viscosity of intestinal contents and the performance of broilers fed rye. Poult. Sci. 70, 1571-1577.
Bedford, M.R., et al. (1993). An in vitro assay for prediction of broiler intestinal viscosity and growth when fed rye-based diets in the presence of exogenous enzymes. Poult. Sci. 72, 137-143.
Bedford, M.R., et al. (1998). Exogenous enzymes for pigs and poultry. Nutr. Res. Rev. 11, 91-114. doi: 10.1079/NRR19980007.
Castanon, J.I. (2007). History of the use of antibiotic as growth promoters in European poultry feeds. Poult. Sci. 86, 2466-2471.
Choct, M., et al. (1995). Nonstarch polysaccharide-degrading enzymes increase the performance of broiler chickens fed wheat of low apparent metabolizable energy. J. Nutr. 125, 485-492.
Choct, M., et al. (1996). Increased small intestinal fermentation is partly responsible for the anti-nutritive activity of non-starch polysaccharides in chickens. Br. Poult. Sci. 37, 609-621.
Cobb-Vantress, Inc. (2013). Cobb 500 broiler performance and nutrition supplement, accessed May 7, 2015, http://www.cobb-vantress.com/products/guidelibrary/ cobbsasso/broiler-performance-and-nutrition-supplement.
Friesen, O. D., et al. "The effect of enzyme supplementation on the apparent metabolizable energy and nutrient digestibilities of wheat, barley, oats, and rye for the young broiler chick." Poultry Science 71.10 (1992): 1710-1721.
Gartman, S.T., et al. (2008). Bacillus subtilis spores germinate in the chicken gastrointestinal tract. Appl. Environ. Microbial. 7 4, 5254-5258.
Gonzalez-Pastor, J.E., et al. (2003). Cannibalism by sporulating bacteria. Science 301, 510-513.
Hoa, T.T., et al. (2001). Fate and dissemination of Bacillus subtilis spores in a murine model. Appl. Environ. Microbial. 67, 3819-3823.
Hong, H.A., et al. (2005). The use of bacterial spore formers as, probiotics. FEMS Microbial. Rev. 29, 813-835.
Hong, H.A., et al. (2009). : Bacillus subtilis isolated from the human gastrointestinal tract. Res. Microbial. 160, , 134-143. doi: 10.1016/j.resmic.2008.11.002.
Huang, J.M., et al. (2010). "Mucosal delivery of antigens using adsorption to bacterial spores." Vaccine 28.4 (2010): 1021-1030.
International Searching Authority, International Search Report and Written Opinion for application PCT/US2016/041977, dated Nov. 14, 2016.
Jadamus, A. et al. "Growth behaviour of a spore forming probiotic strain in the gastrointestinal tract of broiler chicken and piglets." Archives of Animal Nutrition 54.1 (2001): 1-17.
Kiarie, E., et al. (2013). The role of added feed enzymes in promoting gut health in swine and poultry. Nutr. Res. Rev. 26, 71-88. doi: 10.1017/S0954422413000048.
La Ragione, R.M., et al. (2003). "Competitive exclusion by Bacillus subtilis spores of *Salmonella enterica* serotype Enteritidis and Clostridium perfringens in young chickens." Veterinary microbiology 94.3 (2003): 245-256.
Latorre et al. 2013. In Vitro enzyme production and viscosity determination by selective Bacillus spp. in different poultry diets. Symposium on gut health in production of food animals. Kansas City, MO.
Latorre et al. Jul. 14, 2014. Improvement of the nutritive value of rye for neonatal broiler chickens by Direct-fed microbial-induced bacterial translocation and viscosity reduction. Poultry Science Association Annual Meeting. Corpus Christi, Texas.
Latorre et al. Nov. 2014. The role of a selected Bacillus subtilis direct-fed microbial candidate on performance, intestinal viscosity, bacterial translocation and bone mineralization in broiler chickens consuming high NSP diets. Symposium on gut health in production of food animals. St. Louis Missouri.
Latorre, J. D., et al. "Evaluation of germination, distribution, and persistence of Bacillus subtilis spores through the gastrointestinal tract of chickens." Poultry science 93.7 (2014): 1793-1800.
Latorre, J. D., et al. "Selection of Bacillus spp. for cellulase and xylanase production as direct-fed microbials to reduce digesta viscosity and Clostridium perfringens proliferation using an in vitro digestive model in different poultry diets." Frontiers in veterinary science 2 (2015): 25.
Latorre, J. D., et al. "Evaluation and selection of *bacillus* species based on enzyme production, antimicrobial activity, and biofilm synthesis as direct-fed microbial candidates for poultry." Frontiers in veterinary science 3 (2016): 95.

(56) References Cited

OTHER PUBLICATIONS

Latorre, J.D., et al. 2014. Role of a Bacillus subtilis direct-fed microbial on digesta viscosity, bacterial translocation and bone mineralization in neonatal poults fed with a rye-based diet. Front. Vet. Sci. 1 :26.

Layton, S.L., et al. (2013). The effect of a Lactobacillus-based probiotic for the control of necrotic enteritis in broilers. Food Nut. Sci. 4, 1-7.

Lei, X., et al. "Effect of Bacillus amyloliquefaciens-based direct-fed microbial on performance, nutrient utilization, intestinal morphology and cecal microflora in broiler chickens." Asian-Australasian journal of animal sciences 28.2 (2015): 239.

Leser, T.D., et al. (2008). Germination and outgrowth of Bacillus subtilis and Bacillus licheniformis spores in the gastrointestinal tract of pigs. J. Appl. Microbial. 104, 1025-1033.

Li, Y., et al. "Bacillus amyloliquefaciens supplementation alleviates immunological stress in lipopolysaccharide-challenged broilers at early age." Poultry science 94.7 (2015): 1504-1511.

Lopez, D., et al. "Cannibalism enhances biofilm development in Bacillus subtilis." Molecular microbiology 74.3 (2009): 609-618.

Mahmood, K., et al. "Non-antibiotic strategies for the control of necrotic enteritis in poultry." World's Poultry Science Journal 70.4 (2014): 865-879.

McReynolds, J. L., et al. "Evaluation of immunosuppressants and dietary mechanisms in an experimental disease model for necrotic enteritis." Poultry science 83.12 (2004): 1948-1952.

Menconi, A., et al. "Physiological properties and *Salmonella* growth inhibition of probiotic Bacillus strains isolated from environmental and poultry sources." International journal of bacteriology 2013 (2013).

Monisha, R., et al. (2009). Partial purification and characterization of Bacillus pumilus xylanase from soil source. KUSET, 5, 137-148.

Murphy, T. C., et al. "Broiler performance and in vivo viscosity as influenced by a range of xylanases, varying in ability to effect wheat in vitro viscosity." British poultry science 50.6 (2009): 716-724.

Sen, S., et al. (2012). Effect of supplementation of Bacillus subtilis LS 1-2 to broiler diets on growth performance, nutrient retention, caecal microbiology and small intestinal morphology. Res. Vet. Sci. 93, 264-268.

Shirzadi, H. et al. "Influence of non starch polysaccharide-degrading enzymes on the meat yield and viscosity of jejunal digesta in broilers fed wheat/barley-based diet." African Journal of Biotechnology 9.10 (2010): 1517-1522.

Shivaramaiah, S., et al. "Evaluation of *bacillus* species as potential candidates for direct-fed microbials in commercial poultry." Poultry Science 90.7 (2011): 1574-1580.

Slominski, B. A. "Recent advances in research on enzymes for poultry diets." Poultry Science 90.9 (2011): 2013-2023.

Tellez, G., et al. (2012). Probiotics/direct : fed microbials for *Salmonella* control in poultry. Food Res. Int. 45, 628-633.

Tellez, G., et al. (2013). Probiotics for human and poultry use in the control of gastrointestinal disease: a review of real-world experiences. A/tern. Integ. Med. 2, 118. doi: 10.4172/2327-5162.1000118.

Tellez. G., et al. Jan. 2014. Screening of bacteriocins like compounds synthesis from *Bacillus* sp. and the relation between diet composition, viscosity and proliferation of Clostridium perfringens using an in vitro digestive model. International Poultry Scientific Forum in conjunction with the International Poultry Expo, Atlanta. Georgia.

Wang, Z. R., et al. "Effects of enzyme supplementation on performance, nutrient digestibility, gastrointestinal morphology, and volatile fatty acid profiles in the hindgut of broilers fed wheat-based diets." Poultry Science 84.6 (2005): 875-881.

Wolfenden, R. E., et al. "Evaluation of selected direct-fed microbial candidates on live performance and *Salmonella* reduction in commercial turkey brooding houses." Poultry science 90.11 (2011): 2627-2631.

Xu, X., et al. "Immunomodulatory effects of Bacillus subtilis (natto) B4 spores on murine macrophages." Microbiology and immunology 56.12 (2012): 817-824.

Zou, J, et al. "Effects of exogenous enzymes and dietary energy on performance and digestive physiology of broilers." Journal of animal science and biotechnology 4.1 (2013): 14.

Zyla, K., et al. "An in vitro procedure for studying enzymic dephosphorylation of phytate in maize-soyabean feeds for turkey poults." British Journal of Nutrition 74.1 (1995): 3-17.

\* cited by examiner

COMPOSITIONS, PROBIOTIC FORMULATIONS AND METHODS TO PROMOTE DIGESTION AND IMPROVE NUTRITION IN POULTRY

CROSS-REFERENCE TO RELATED APPLICATIONS

This patent application is a national stage filing under 35 U.S.C. 371 of International Application No. PCT/US2016/041977, filed Jul. 13, 2016, which claims the benefit of priority of U.S. Provisional Patent Application No. 62/192,501, filed Jul. 14, 2015, both of which are incorporated herein by reference in their entirety.

BACKGROUND

Field of the Disclosure

Probiotic compositions, formulations and methods are disclosed, including methods for promoting digestion and improving nutrition in birds.

Description of the Related Art

Feedstuffs used for nutrition of monogastric agricultural animals (e.g. poultry, swine, aqua) contain a large percentage of non-digestible nutrients. These include non-starch polysaccharides (NSP; for example fiber), phytates and damaged proteins. These ingredients can be "wasted" as sources of energy or other nutrients for such animals. These can interfere with access of the animal's digestive enzymes for absorption of digestible nutrients. For example, non-digestible feed components can cause opportunistic pathogen overgrowth within the gastrointestinal tract, leading to gut inflammation, problems with absorption of nutrients, bacterial leakage across the mucosal epithelium causing either systemic infections or toxemias, and overall poor performance (principally evaluated by measuring body weight gain and feed efficiency). Problems associated with poor digestibility of feed can cause chronic low level to severe flushing (diarrhea). These can lead to environmental problems, including air quality and ammonia generation, which further contribute to animal health primarily by affecting the respiratory tract or skin of the animals.

High levels of NSP and/or damaged proteins are frequently a problem when some grains are substituted for corn. Wheat, barley, and rye, among others, contain very high levels of NSP. Intake of the grains in animals tends to increase digesta viscosity and gut inflammation and can cause an overgrowth of disadvantageous microflora in the gut (dysbiosis). Dysbiosis is often predisposing to serious gastrointestinal states, such as necrotic enteritis or colibacillosis which can cause high morbidity and mortality in animals.

Animal feed can be supplemented with low level feeding of certain antibiotics, referred to as antibiotic growth promotors (AGP). These have traditionally been used to control secondary gut health issues, such as to reduce enteric inflammation and to enhance food performance. Currently, there is growing social and regulatory pressures to remove these drugs from diets.

During the last two decades, a number of biosynthetic, exogenously produced enzyme products have been developed for inclusion in the diets of monogastric animals. Phytases, which break down non-digestible phytate sources of phosphorous, have been used widely to reduce the necessary mineral phosphorous added to the diets. This treatment has a further benefit of reducing phosphorous in the manure, thereby reducing the environmental impact of phosphorus generally.

More recently, other biosynthetic enzymes have been used to attack other non-digestible substrates. These include products containing enzymes that attack or breakdown non-starch polysaccharides (NSPase), hemicellulose (hemicellulase), xylan (xylanases), protein (proteases), and others.

These enzymes are thought to increase flexibility of feed ingredient selection, in some cases reducing the cost of feed formulation.

Probiotic compositions or formulations for promoting the digestion of feed would be advantageous.

SUMMARY

Probiotic compositions, formulations and methods for promoting digestion and improving nutrition in birds are provided. Variously described probiotic compositions and formulations for increasing enzyme production and improving various parameters or indications in birds are further provided.

In an aspect, a probiotic composition for improving digestion of nutrients in an animal includes at least two enzyme producing *Bacillus* isolates selected from *Bacillus amyloliquefaciens* JD17 (NRRL Deposit B-67142), *Bacillus licheniformis* AM1002 (NRRL Deposit B-67143), *Bacillus amyloliquefaciens* AM0938 (NRRL Deposit B-67144), *Bacillus amyloliquefaciens* AM1109B (NRRL Deposit B-67146), *Bacillus amyloliquefaciens* AM1101 (NRRL Deposit B-67147), *Bacillus amyloliquefaciens* AM0939 (NRRL Deposit B-67148), *Bacillus amyloliquefaciens* AM0934 (NRRL Deposit B-67149), *Bacillus amyloliquefaciens* AM0933 (NRRL Deposit B-67277), *Bacillus amyloliquefaciens* AM0940 (NRRL Deposit B-67278), or any combination thereof, and an agriculturally acceptable excipient.

In another aspect, the enzyme producing *Bacillus* isolates produce one or more of enzymes or substances having phytase, protease, lipase, cellulase, or xylanase activity, or any combination thereof. In embodiments, the enzyme producing *Bacillus* isolates form a biofilm. In embodiments, the enzyme producing *Bacillus* isolates are spore forming *Bacillus*, where the spore forming *Bacillus* produces e.g. at least about $1 \times 10^4$ to about $1 \times 10^{11}$ spores per gram of fermentate, such as at least about $1 \times 10^4$ to about $1 \times 10^5$ spores per gram of fermentate, for example at least about $1 \times 10^5$ to about $1 \times 10^6$ spores per gram of fermentate, such as at least about $1 \times 10^6$ to about $1 \times 10^7$ spores per gram of fermentate, for example at least about $1 \times 10^7$ to about $1 \times 10^8$ spores per gram of fermentate, such as at least about $1 \times 10^8$ to about $1 \times 10^9$ spores per gram of fermentate, for example at least about $1 \times 10^9$ to about $1 \times 10^{10}$ spores per gram of fermentate, such as at least about $1 \times 10^{10}$ to about $1 \times 10^{11}$ spores per gram of fermentate, or any combination of these intervals.

In another aspect, enzyme producing *Bacillus* isolates herein are provided in an animal feed. The isolates may be added to animal feed during a pelleting process, for example. In embodiments, the animal feed is a pelletized bird feed. In embodiments, the animal feed comprises any of corn, soybean, rye, barley, wheat, oats, sorghum, distiller's dried grains with solubles, or any combination thereof.

In another aspect, a probiotic formulation is provided comprising the enzyme producing *Bacillus* isolates herein at a concentration of about $1 \times 10^4$ to about $1 \times 10^{10}$ colony forming units (cfu) of spores per gram of animal feed such as at least about $1\times10^4$ to $1\times10^5$ cfu of bacterial spores per gram of animal feed, for example at least about $1\times10^5$ to $1\times10^6$ cfu of bacterial spores per gram of animal feed, such as at least about $1\times10^6$ to $1\times10^7$ cfu of bacterial spores per gram of animal feed, for example at least about $1\times10^7$ to $1\times10^8$ cfu of bacterial spores per gram of animal feed, such as at least about $1\times10^8$ to $1\times10^9$ cfu of bacterial spores per gram of animal feed, for example at least about $1\times10^9$ to $1\times10^{10}$ cfu of bacterial spores per gram of animal feed or any combination of these intervals.

In another aspect, a probiotic composition for improving digestion of nutrients in an animal includes at least two enzyme producing *Bacillus* isolates selected from *Bacillus amyloliquefaciens* JD17 (NRRL Deposit B-67142), *Bacillus licheniformis* AM1002 (NRRL Deposit B-67143), *Bacillus amyloliquefaciens* AM0938 (NRRL Deposit B-67144), *Bacillus amyloliquefaciens* AM1109B (NRRL Deposit B-67146), *Bacillus amyloliquefaciens* AM1101 (NRRL Deposit B-67147), *Bacillus amyloliquefaciens* AM0939 (NRRL Deposit B-67148), *Bacillus amyloliquefaciens* AM0934 (NRRL Deposit B-67149), *Bacillus amyloliquefaciens* AM0933 (NRRL Deposit B-67277) and *Bacillus amyloliquefaciens* AM0940 (NRRL Deposit B-67278), wherein at least one isolate produces one or more of enzyme or substance comprising phytase, protease, lipase, cellulose, or xylanase activity. In embodiments, at least two enzyme producing isolates are provided which produce one or more of enzymes or substances comprising phytase, protease, lipase, cellulase, or xylanase activity, wherein each bacteria may produce the same or a different enzyme. In further embodiments, one or more isolates produce at least two enzymes or substances, and each enzyme is produced in differing concentrations.

In another aspect, enzyme producing *Bacillus* bacterial isolates are provided which improve digestion of nutrients in an animal, where the improved digestion of nutrients corresponds to an increase in one or more parameters or indications. In embodiments, the improvement includes one or more of increased body weight, and/or increased bone strength and/or improved bone composition, where the bone composition may be measured as total ash, calcium content and/or phosphorus content.

In another aspect, a method for improving digestion of nutrients in an animal is provided, the method comprising providing a probiotic composition to an animal comprising at least two enzyme producing *Bacillus* bacterial isolates selected from a probiotic composition for improving digestion of nutrients in an animal includes at least two enzyme producing *Bacillus* isolates selected from *Bacillus amyloliquefaciens* JD17 (NRRL Deposit B-67142), *Bacillus licheniformis* AM1002 (NRRL Deposit B-67143), *Bacillus amyloliquefaciens* AM0938 (NRRL Deposit B-67144), *Bacillus amyloliquefaciens* AM1109B (NRRL Deposit B-67146), *Bacillus amyloliquefaciens* AM1101 (NRRL Deposit B-67147), *Bacillus amyloliquefaciens* AM0939 (NRRL Deposit B-67148), *Bacillus amyloliquefaciens* AM0934 (NRRL Deposit B-67149), *Bacillus amyloliquefaciens* AM0933 (NRRL Deposit B-67277), *Bacillus amyloliquefaciens* AM0940 (NRRL Deposit B-67278), or any combination thereof, and an agriculturally acceptable excipient.

In another aspect, a method of improving one or more parameters or indications is provided, where the method comprises providing one or more *Bacillus* isolates to an animal, and where the one or more parameters or indications comprises one or more of body weight, feed intake, feed conversion ratio, bone strength, bone composition, viscosity, and/or bacterial translocation. In embodiments the isolates are provided in animal feed. In embodiments, the animal feed comprises at least one of corn, soybean, rye, barley, wheat, oats, sorghum, distiller's dried grains with solubles, or any combination thereof.

In another aspect, a method for selecting an enzyme producing bacterial isolate is provided, the method including: a) identifying at least one bacterial isolate capable of producing one or more enzymes; b) determining biofilm production in at least one bacterial isolate selected from step a); c) identifying at least one bacterial isolate from step b) capable of forming spores; and d) selecting at least one bacterial isolate from step c) wherein at least one bacterial isolate is capable of improving one or more digestion related parameters or indications.

BRIEF DESCRIPTION OF THE DRAWINGS

FIG. 2A, viscosity of corn-soybean, wheat-soybean and barley-soybean. FIG. 2B, viscosity of rye-soybean and oats-soybean.

FIG. 3B shows that energy uptake was improved by 0.2 kcal/gram.

DETAILED DESCRIPTION

Figure 1:
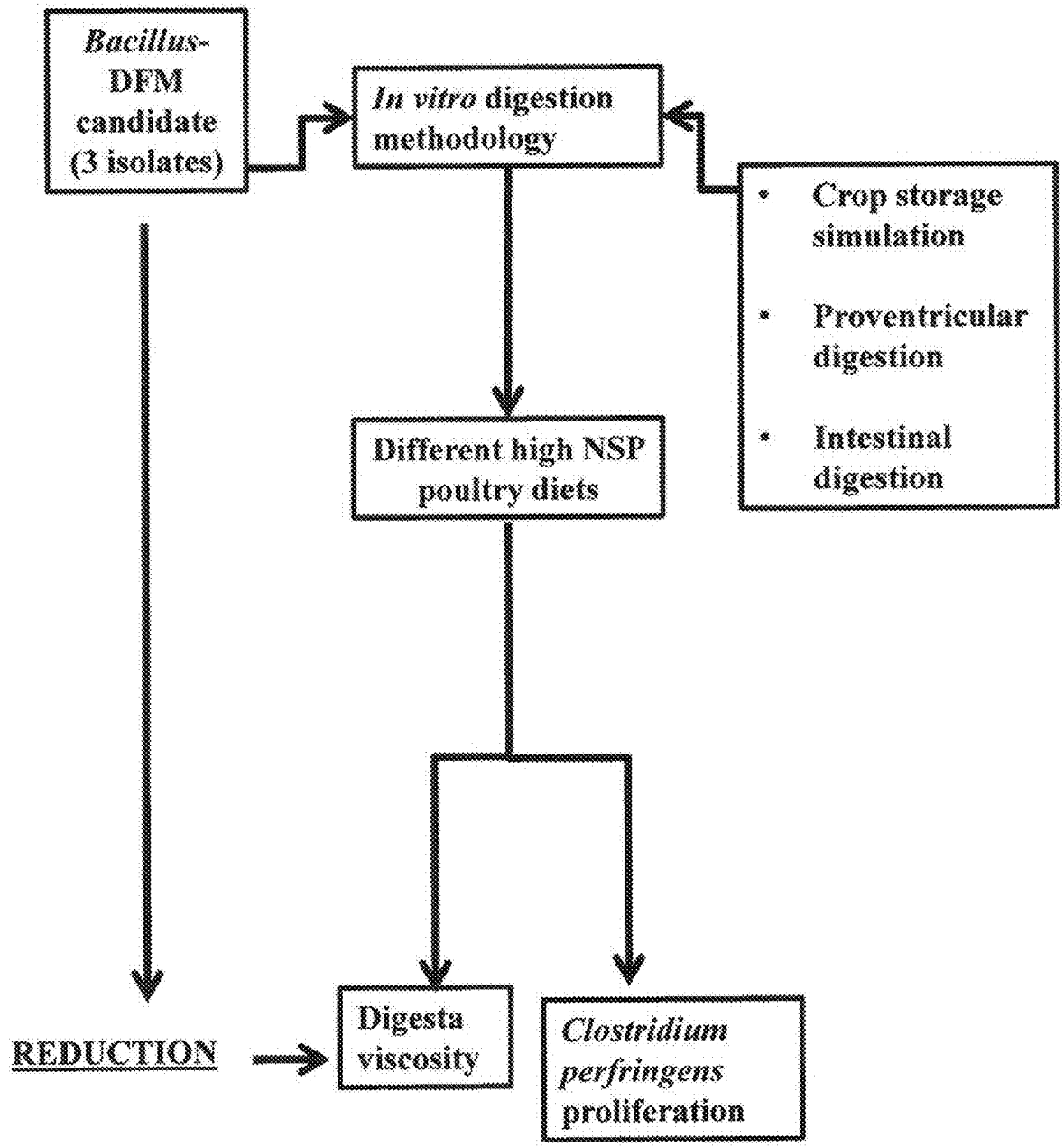
FIG. 1 illustrates an in vitro digestion methodology.

The following description is merely exemplary in nature and is not intended to limit the present invention, its applications, or its uses. It should be understood that throughout the drawings, corresponding reference numerals indicate like or corresponding parts and features. The description of specific examples indicated in various embodiments of the present invention are intended for purposes of illustration only and are not intended to limit the scope of the invention disclosed herein. Moreover, recitation of multiple embodiments having stated features is not intended to exclude other embodiments having additional features or other embodiments incorporating different combinations of the stated features.

Furthermore, the detailed description of various embodiments herein makes reference to the accompanying drawing FIGS, which show various embodiments by way of illustration. While the embodiments are described in sufficient detail to enable those skilled in the art to practice the invention, it should be understood that other embodiments may be realized and that logical and mechanical changes may be made without departing from the spirit and scope of the present invention. Thus, the detailed description herein is presented for purposes of illustration only and not of limitation. For example, steps or functions recited in descriptions, any method, system, or process, may be executed in any order and are not limited to the order presented. Moreover, any of the step or functions thereof may be outsourced to or performed by one or more third parties. Furthermore, any reference to singular includes plural embodiments, and any reference to more than one component may include a singular embodiment.

I. Definitions

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the subject matter of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

The term "about" means a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this disclosure, unless the context requires otherwise, the words "comprise," "comprises," and "comprising" will be understood to imply the inclusion of a stated step or element or group of steps or elements but not the exclusion of any other step or element or group of steps or elements.

The term "consisting of" means including, and limited to, whatever follows the phrase "consisting of." Thus, the phrase "consisting of" indicates that the listed elements are required or mandatory, and that no other elements may be present. The term "consisting essentially of" means including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

As used herein, a "bird" may include a neonatal bird or an adult bird. A bird may be poultry, including, but not limited to, a chicken, a turkey, a duck, a goose, or a pheasant.

As used herein, the terms "bioequivalent" or "bioequivalence" refer to a probiotic composition or formulation that has been shown to be efficacious in vivo and has been shown to be bioequivalent to a reference standard. A reference standard may be a commercially available probiotic composition or formulation.

As used herein, the terms "body weight" (BW) or "body weight gain" (BWG) may include a change, either a decrease or an increase, in the body weight or body weight gain of an animal. The body weight or body weight gain of an animal may be measured in grams (g). An animal provided a feed including a probiotic composition or formulation may demonstrate an increase in body weight or body weight gain compared to the body weight or body weight gain of an animal provided a feed without a probiotic composition or formulation.

As used herein, the term "bacterial translocation" may refer to the crossing of an animal's intestinal barrier by bacteria. In a well-functioning gut, bacteria are prevented from crossing the intestinal barrier. Bacterial translocation may be measured as the number of cfu of bacteria (for example, *Escherichia coli*) detected in a sample of liver tissue. The number of cfu's may be expressed as cfu $Log_{10}$ per gram of liver tissue.

As used herein, the terms "bone strength" or "bone breaking strength" may be a measure of the strength required to break a bone of an animal. Bone strength may be measured as tibia strength load at yield in $kg/mm^2$.

As used herein, the terms "bone composition" or "bone content" may refer to the material from which a bone is composed. The material may include ash and mineral components, for example, calcium and phosphorus. Bone composition or bone content may be measured as the total percent of ash from a tibia bone of an animal. The mineral components or content may be measured as the percent of calcium and/or the percent of phosphorus in the ash from a tibia bone.

As used herein, the term "feed conversion ratio" is a measurement for the conversion of feed to body weight. The feed conversion ratio may be measured as the feed intake in grams divided by the body weight in grams of an animal. An improvement, for example, measured as a decrease in the feed conversion ratio may be attributed to improved absorption of nutrients by the animal.

As used herein, the term "feed intake" may include the amount of feed ingested by an animal during regular feeding intervals. The feed intake of an animal may be measured as the amount of feed in grams ingested by an animal. The feed intake of an animal may decrease in an animal provided a feed that includes a probiotic composition or formulation without a negative or detrimental effect to body weight or body weight gain of the animal. A reduction in feed intake may correspond with an increase in body weight or body weight gain in an animal provided a feed that includes a probiotic composition or formulation.

As used herein, the terms "intestinal viscosity," "digesta viscosity" or "viscosity" may include the measure of a substance's resistance to degradation by shear or tensile stress, or a measure of the thickness of a substance, or the measure of a fluid's resistance to flow. Intestinal viscosity, digesta viscosity or viscosity may be measured as centipoise (cP; for example, 1 cP=$10^{-2}$ P=$10^{-3}$ Pa·s=1 mPa·s; P is Poise, Pa·s is pascal second, mPa·s is mili pascal second). Viscosity may be measured using methods known to those of ordinary skill in the art, for example, a cone/plate viscometer.

A "decreased" or "reduced" amount is typically a "statistically significant" amount, and may include a decrease that is 1, 2, 3, 4, 5, 6, 7, 8, 9, 10, 15, 20, 30, 40, 50 or more times less (e.g., 100, 500, 1000 times), including all integers and decimal points in between and above 1 (e.g., 1.1, 1.2, 1.3, 1.4, 1.5, 1.6, 1.7, 1.8, 1.9), the amount produced by an animal in the absence of a probiotic composition or formulation, for example, feed without a probiotic composition or formulation (e.g. the "native" or "natural" feed intake, feed conversion rate, intestinal viscosity, or bacterial translocation).

A "decrease" in a response may be "statistically significant" as compared to the response produced by an animal in the absence of a probiotic composition or formulation, for example, feed without a probiotic composition or formulation (e.g. the "native" or "natural" feed intake, feed conversion rate, intestinal viscosity, or bacterial translocation), and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

A "improvement" or "increased amount" amount is typically a "statistically significant" improvement or amount, and may include an improvement or increase that is 1, 2, 3, 4, 5, 6, 7, 8, 9, 10, 15, 20, 30, 40, 50 or more times more (e.g., 100, 500, 1000 times), including all integers and decimal points in between and above 1 (e.g., 1.1, 1.2, 1.3, 1.4, 1.5, 1.6, 1.7, 1.8, 1.9), the amount produced by an animal in the absence of a probiotic composition or formulation, for example, feed without a probiotic composition or formulation (e.g. the "native" or "natural" feed intake, feed conversion rate, intestinal viscosity, or bacterial translocation).

An "increase" in a response may be "statistically significant" as compared to the response produced by an animal in the absence of a probiotic composition or formulation, for example, feed without a probiotic composition or formulation (e.g. the "native" or "natural" body weight gain, bone strength and bone composition), and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% increase, including all integers in between.

The term "isolated" refers to a material that is substantially or essentially free from components that normally accompany it in its native state. For example, an isolated *Bacillus* isolate may refer to a *Bacillus* isolate that has been purified or removed from naturally or non-naturally occurring components that are present in its naturally occurring environment.

The term "modulate" includes to "increase" or "decrease" one or more quantifiable parameters or indications, optionally by a defined and/or statistically significant amount. By "increase" or "increasing," "enhance" or "enhancing," or "stimulate" or "stimulating," refers generally to the ability of a probiotic composition or formulation to produce or cause a greater physiological response (e.g., downstream effects) in an animal relative to the response caused by a control formulation, for example, feed without a probiotic composition or formulation. Relevant physical responses will be apparent to persons skilled in the art, and may include one or more of an increase in body weight, bone strength and bone composition in an animal. By "decrease" or "decreasing," "reduce" or "reducing," refers generally to the ability of a probiotic composition or formulation to produce a lesser physiological response in an animal relative to the response caused by a control formulation. Relevant physical responses will be apparent to persons skilled in the art, and may include one or more of a decrease in feed intake, feed conversion ratio, intestinal viscosity or bacterial translocation in an animal. An "increased" or "enhanced" amount is typically a "statistically significant" amount, and may include an increase that is 1, 2, 3, 4, 5, 6, 7, 8, 9, 10, 15, 20, 30, 40, 50 or more times more (e.g., 100, 500, 1000 times), including all integers and decimal points in between and above 1 (e.g., 1.1, 1.2, 1.3, 1.4, 1.5, 1.6, 1.7, 1.8, 1.9), the amount produced by an animal in the absence of a probiotic composition or formulation (e.g. the "native" or "natural" body weight gain, bone strength and bone composition of an animal). A "decreased" or "reduced" amount is typically a "statistically significant" amount, and may include a decrease that is 1, 2, 3, 4, 5, 6, 7, 8, 9, 10, 15, 20, 30, 40, 50 or more times less (e.g., 100, 500, 1000 times), including all integers and decimal points in between and above 1 (e.g., 1.1, 1.2, 1.3, 1.4, 1.5, 1.6, 1.7, 1.8, 1.9), the amount produced by an animal in the absence of a probiotic composition or formulation (e.g. the "native" or "natural" body feed intake, feed conversion ratio, viscosity or bacterial translocation of an animal).

As used herein, the terms "non-digestible" or "difficult to digest" refers to a compound or nutrient that passes undigested through the gastrointestinal tract of an animal. Digestion is the breakdown of large insoluble molecules in feed into small water-soluble molecules or nutrients such that they may be absorbed via the gastrointestinal tract. A non-digestible or difficult to digest nutrient may lead to gastrointestinal issues in an animal. A probiotic composition or formulation may increase the digestibility of non-digestible or difficult to digest nutrients and improve nutrition, nutrient availability and nutrient absorption in an animal.

A "similar" response may be a response caused in an animal provided a probiotic composition or formulation that is not statistically significant or statistically different than the response produced by an animal in the absence of a probiotic composition or formulation, for example, feed without a probiotic composition or formulation (e.g. the "native" or "natural" feed intake, feed conversion rate).

As used herein, the terms "quantifying," "quantification" or other related words refer to determining the quantity, mass, or concentration in a unit volume, of a parameter or indication, for example, body weight, feed intake, feed conversion rate, bone strength, bone composition, intestinal viscosity and bacterial translocation.

As used herein, the term "fermentate" is generally understood to mean a bacterial fermentation product that may contain only the bacteria, only the bacterial spores or the bacterial and/or spores along with the products of fermentation.

II. Compositions and Formulations

In aspects, a probiotic composition or formulation of the present disclosure may improve, enhance and/or facilitate digestion of nutrients in an animal. In embodiments, the composition or formulation includes at least one enzyme producing bacterial isolate.

In embodiments, an enzyme producing bacterial isolate is provided which produces enzymes or substances having enzymatic activity. In further embodiments, the enzymatic activity is capable of breaking down macromolecule nutrients in animal feed. A macromolecule nutrient includes, but is not limited to, non-starch polysaccharides (NSP; for example, fiber), phytate (for example, phytic acid), protein, lipids (for example, fats, including saturated and unsaturated fats), and carbohydrates (for example, polysaccharides, cellulose, xylan). In embodiments, a bacterial isolate produces one or more enzymes, for example, phytase, protease, lipase, cellulase, and xylanase.

In embodiments, a bacterial isolate may produce one or more of enzymes having phytase, protease, lipase, cellulase, or xylanase activity, or any combination thereof. In embodiments, the bacterial isolate may be a *Bacillus* isolate. In further embodiments, the *Bacillus* isolate may produce one or more enzymes having higher enzymatic activity against a macromolecule nutrient and one or more enzymes having lower enzymatic activity against a macromolecule nutrient.

A *Bacillus* isolate may include, but is not limited to, *Bacillus subtilis*, *Bacillus amyloliquefaciens*, *Bacillus licheniformis*, *Bacillus amyloliquefaciens*, or any combination thereof. In embodiments, at least one *Bacillus* isolate is selected from a probiotic composition for improving digestion of nutrients in an animal includes at least two enzyme producing *Bacillus* isolates selected from *Bacillus amyloliquefaciens* JD17 (NRRL Deposit B-67142), *Bacillus licheniformis* AM1002 (NRRL Deposit B-67143), *Bacillus amyloliquefaciens* AM0938 (NRRL Deposit B-67144), *Bacillus amyloliquefaciens* AM1109B (NRRL Deposit B-67146), *Bacillus amyloliquefaciens* AM1101 (NRRL Deposit B-67147), *Bacillus amyloliquefaciens* AM0939 (NRRL Deposit B-67148), *Bacillus amyloliquefaciens* AM0934 (NRRL Deposit B-67149), *Bacillus amyloliquefaciens* AM0933 (NRRL Deposit B-67277), *Bacillus*

*amyloliquefaciens* AM0940 (NRRL Deposit B-67278), or any combination of the foregoing. In embodiments, at least one *Bacillus* isolate is selected from the foregoing. In embodiments, at least two *Bacillus* isolates are selected from the foregoing. In embodiments, at least three *Bacillus* isolates are selected from the foregoing. The bacterial isolates have been deposited with Agricultural Research Service Culture Collection (NRRL), 1815 North University Street, Peoria, Ill. 61604, U.S.A., under suitable accession numbers.

In embodiments, the *Bacillus* isolates comprise at least two of *Bacillus amyloliquefaciens* AM0938 (NRRL Deposit B-67144) and *Bacillus amyloliquefaciens* JD17 (NRRL Deposit B-67142).

In embodiments, the *Bacillus* isolates comprise at least two of *Bacillus amyloliquefaciens* AM1002 (NRRL Deposit B-67143), *Bacillus amyloliquefaciens* AM0938 (NRRL Deposit B-67144), and *Bacillus amyloliquefaciens* JD17 (NRRL Deposit B-67142). In further embodiments, the *Bacillus* isolates comprise at least three of *Bacillus licheniformis* AM1002 (NRRL Deposit B-67143), *Bacillus amyloliquefaciens* AM0938 (NRRL Deposit B-67144), and *Bacillus amyloliquefaciens* JD17 (NRRL Deposit B-67142).

In embodiments, the *Bacillus* isolates comprise at least two of *Bacillus amyloliquefaciens* AM0938 (NRRL Deposit B-67144), *Bacillus amyloliquefaciens* JD17 (NRRL Deposit B-67142) and *Bacillus amyloliquefaciens* AM0939 (NRRL Deposit B-67148). In further embodiments, the *Bacillus* isolates comprise at least three of *Bacillus amyloliquefaciens* AM0938 (NRRL Deposit B-67144), *Bacillus amyloliquefaciens* JD17 (NRRL Deposit B-67142) and *Bacillus amyloliquefaciens* AM0939 (NRRL Deposit B-67148).

A probiotic composition or formulation may include one or more *Bacillus* isolates selected from any of the foregoing. In embodiments, the composition or formulation includes one or more of *Bacillus licheniformis* AM1002 (NRRL Deposit B-67143), *Bacillus amyloliquefaciens* AM0938 (NRRL Deposit B-67144) and *Bacillus amyloliquefaciens* JD17 (NRRL Deposit B-67142), or any combinations thereof.

In embodiments, a *Bacillus* isolate is a spore forming bacteria, for example, a bacteria capable of sporulation. In embodiments, the spore forming *Bacillus* is able to withstand and survive variable conditions, for example, high heat, chemicals, radiation, hyper and hypo tonicity, pH changes, and environmental conditions, for example, as may be found under various animal feed pelleting and other manufacturing processes, or as may be found within the gastrointestinal tract of an animal. In embodiments, the *Bacillus* isolate produces at least about $1\times10^4$ to $1\times10^{11}$ spores per gram of fermentate, such as at least about $1\times10^4$ to about $1\times10^5$ spores per gram of fermentate, for example at least about $1\times10^5$ to about $1\times10^6$ spores per gram of fermentate, such as at least about $1\times10^6$ to about $1\times10^7$ spores per gram of fermentate, for example at least about $1\times10^7$ to about $1\times10^8$ spores per gram of fermentate, such as at least about $1\times10^8$ to about $1\times10^9$ spores per gram of fermentate, for example at least about $1\times10^9$ to about $1\times10^{10}$ spores per gram of fermentate, such as at least about $1\times10^{10}$ to about $1\times10^{11}$ spores per gram of fermentate, or any combination of these intervals. In embodiments, the *Bacillus* isolate produces at least about $1\times10^4$, $1\times10^5$, $1\times10^6$, $1\times10^7$, $1\times10^8$, $1\times10^9$, or $1\times10^{10}$ spores per gram of fermentate.

In various embodiments, a *Bacillus* isolate is a direct-fed microbial (DFM). In embodiments, a direct fed microbial is a source of live (viable) naturally occurring microorganisms supplied through the feed. In embodiments, a *Bacillus* direct-fed microbial includes at least one of a a probiotic composition for improving digestion of nutrients in an animal includes at least two enzyme producing *Bacillus* isolates selected from *Bacillus amyloliquefaciens* JD17 (NRRL Deposit B-67142), *Bacillus licheniformis* AM1002 (NRRL Deposit B-67143), *Bacillus amyloliquefaciens* AM0938 (NRRL Deposit B-67144), *Bacillus amyloliquefaciens* AM1109B (NRRL Deposit B-67146), *Bacillus amyloliquefaciens* AM1101 (NRRL Deposit B-67147), *Bacillus amyloliquefaciens* AM0939 (NRRL Deposit B-67148), *Bacillus amyloliquefaciens* AM0934 (NRRL Deposit B-67149), *Bacillus amyloliquefaciens* AM0933 (NRRL Deposit B-67277), *Bacillus amyloliquefaciens* AM0940 (NRRL Deposit B-67278), or any combination thereof.

In various embodiments, the probiotic compositions or formulations may be administered in drinking water or may be incorporated into animal feed. In embodiments, at least one enzyme producing bacterial isolate of the probiotic composition or formulation is capable of surviving feed process and preparation methods. In embodiments, the bacterial isolates retain enzyme activity after exposure to the conditions used during the feed process. In some embodiments, the bacterial isolates retain enzyme activity after exposure to high temperatures used during and after the pelleting stage of the feed process. In embodiments, the probiotic compositions or formulations may be incorporated into an animal feed prior to, during, or after the pelleting stage of the feed process. In embodiments, the probiotic composition or formulation may be incorporated into bird feed.

In various embodiments, the probiotic compositions or formulations may be formulated as a dry powder, suspension or solution. The probiotic compositions or formulations may be delivered in water, by oral gavage or aerosol spray, or may be incorporated into animal feed as a dry powder, suspension or solution. The animal feed may comprise a probiotic composition or formulation including about $1\times10^4$ to $1\times10^{10}$ cfu of bacterial spores per gram of animal feed such as at least about $1\times10^4$ to $1\times10^5$ cfu of bacterial spores per gram of animal feed, for example at least about $1\times10^5$ to $1\times10^6$ cfu of bacterial spores per gram of animal feed, such as at least about $1\times10^6$ to $1\times10^7$ cfu of bacterial spores per gram of animal feed, for example at least about $1\times10^7$ to $1\times10^8$ cfu of bacterial spores per gram of animal feed, such as at least about $1\times10^8$ to $1\times10^9$ cfu of bacterial spores per gram of animal feed, for example at least about $1\times10^9$ to $1\times10^{10}$ cfu of bacterial spores per gram of animal feed or any combination of these intervals. The animal feed may comprise a probiotic composition or formulation including about $1\times10^4$, about $1\times10^5$, about $1\times10^6$, about $1\times10^7$, about $1\times10^8$, about $1\times10^9$ or about $1\times10^{10}$ cfu of bacterial spores per gram of animal feed. The animal feed may comprise a probiotic composition or formulation including at least one bacterial isolate or a combination of two or more bacterial isolates.

In various embodiments, the probiotic compositions or formulations may be formulated for oral administration. The probiotic compositions or formulations may be formulated for ingestion via animal feed.

In various aspects, an animal feed may comprise one or more of corn, soybean, rye, barley, wheat, oats, sorghum, distiller's dried grains with solubles (DDGS; or other ethanol byproduct), or any combination thereof. The animal feed may comprise one or more of corn, soybean, rye, barley, wheat, oats, and sorghum in various amounts. The animal feed may, for example, comprise about 5%, about 6%, about 7%, about 8%, about 9%, about 10%, about 11%, about 12%, about 13%, about 14%, about 15%, about 16%, about 17%, about 18%, about 19% about 20%, about 25%, about 30%, about 35%, about 40%, about 45%, about 50%, about 55%, about 60%, about 65%, about 70%, about 75%, about 80%, about 85%, about 90%, about 95%, about 99% or about 100%, including all integers in between, of any one or more of corn, soybean, rye, barley, wheat, oats, sorghum, or DDGS.

One of skill in the art will recognize that probiotic compositions and formulations are routinely designed according to their intended use, i.e. route of administration.

III. Formulations

In various aspects, at least one enzyme producing bacterial isolate may be formulated as a probiotic formulation. In embodiments, the probiotic formulation may be formulated as a dry powder, suspension or solution. In embodiments, the probiotic formulation formulated as a dry powder may be soluble in water. In embodiments, the probiotic formulation formulated as a dry powder may be soluble in an organic solvent. In embodiments, the probiotic formulation formulated as a dry powder may be directly added to an animal feed during processing and manufacturing.

In various aspects, the formulation of the present disclosure may include an agriculturally acceptable excipient. In embodiments, an agriculturally acceptable carrier may be solid, liquid or both. In embodiments, solid carriers may be mineral earth for example, silicas, silica gels, silicates, talc, kaolin, montmorillonite, attapulgite, pumice, sepiolite, bentonite, limestone, lime, chalk, bole, loes, clay, dolomite, diatomaceous earth, calcite, calcium sulfate, magnesium sulfate, magnesium sulfate, magnesium oxide, sand, ground plastics, fertilizers for example ammonium sulfate, ammonium phosphate, ammonium nitrate, ureas, and crushed products of vegetable origin such as cereal meal, tree bark meal, wood meal and nutshell meal, cellulose powders, or other solid carriers.

In embodiments, a formulation may optionally include surfactant(s). In embodiments, a surfactant may be non-ionic, cationic and/or anionic in nature, and surfactant mixtures that have emulsifying, dispersing and wetting properties, depending on the nature of the active ingredient to be formulated. In embodiments, anionic surfactants may be both water-soluble soaps and water-soluble synthetic surface-active compounds. In embodiments, soaps may be alkali metal, alkaline earth metal or substituted or unsubstituted ammonium salts of higher fatty acids (C10-C22), for example the sodium or potassium salt of oleic or stearic acid, or of natural fatty acid mixtures.

In embodiments, a probiotic formulation may include an oil, for example, mineral oil. In embodiments, a probiotic formulation may include rice hulls, wheat bran, calcium carbonate, mineral oil, or any combination thereof. In embodiments, a dry form probiotic formulation of the present disclosure is included in an animal food. In embodiment, the dry form probiotic formulation includes about $1\times10^6$ bacterial spores per gram of animal feed. In embodiments, the dry form probiotic formulation is added to an animal feed at about 0.5 lb, 1.0 lb, 1.5 lb, or 2.0 lb of dry form probiotic formulation per ton of animal feed. In embodiments, the dry form probiotic formulation may be added to or mixed with other agriculturally acceptable excipients disclosed herein before added to an animal feed.

IV. Enzyme Producing Isolates

In various aspects, one or more enzyme producing *Bacillus* isolates including at least one a probiotic composition for improving digestion of nutrients in an animal includes at least two enzyme producing *Bacillus* isolates selected from *Bacillus amyloliquefaciens* JD17 (NRRL Deposit B-67142), *Bacillus licheniformis* AM1002 (NRRL Deposit B-67143), *Bacillus amyloliquefaciens* AM0938 (NRRL Deposit B-67144), *Bacillus amyloliquefaciens* AM1109B (NRRL Deposit B-67146), *Bacillus amyloliquefaciens* AM1101 (NRRL Deposit B-67147), *Bacillus amyloliquefaciens* AM0939 (NRRL Deposit B-67148), *Bacillus amyloliquefaciens* AM0934 (NRRL Deposit B-67149), *Bacillus amyloliquefaciens* AM0933 (NRRL Deposit B-67277), *Bacillus amyloliquefaciens* AM0940 (NRRL Deposit B-67278) or any combination thereof. In embodiments, an enzyme producing *Bacillus* isolate produces one or more of enzymes or substances having phytase, protease, lipase, cellulase, xylanase activity, or any combination thereof.

In aspects, one or more enzyme producing *Bacillus* isolates improve, enhance and/or facilitate digestion or digestibility of nutrients in an animal. In embodiments, improved digestion or digestibility of nutrients corresponds to an increase or decrease in one or more parameters or indications. In embodiments, one or more parameters or indications includes body weight, bone strength, bone composition, feed intake, feed conversion ratio, viscosity and/or bacterial translocation.

In embodiments, one or more enzyme producing *Bacillus* isolates are provided in animal feed to increase body weight, improve bone strength and/or improve bone composition in the animal. In embodiments, bone composition may be measured as total ash. In embodiments, bone composition may be measured as mineral content. In embodiments, mineral content may be measured as the percent of calcium and/or the percent of phosphorus in ash from a bone.

In embodiments, one or more enzyme producing *Bacillus* isolates are provided in animal feed to decrease the feed conversion ratio, intestinal viscosity and/or bacterial translocations.

In embodiments, one or more enzyme producing *Bacillus* isolates produce one or more enzymes capable of breaking down at least one macromolecule nutrient in an animal feed. In various embodiments, a *Bacillus* isolate produces at least one enzyme or substance having phytase, protease, lipase, cellulase, xylanase, or any combination thereof, or produces one or more enzyme or substance having phytase, protease, lipase, cellulase, or xylanase activity. In embodiments, a macromolecule nutrient includes, but is not limited to, non-starch polysaccharides (NSP; for example, fiber), phytate (for example, phytic acid) protein, lipids (for example, fats, including saturated and unsaturated fats), and carbohydrates (for example, polysaccharides).

In embodiments, one or more enzyme producing *Bacillus* isolates set forth herein are provided in a probiotic composition or formulated as a probiotic formulation. In embodiments, the probiotic composition or formulation is provided in animal feed. In embodiments, the animal feed may comprise a probiotic composition or formulation including about $1\times10^4$ to $1\times10^{10}$ cfu of *Bacillus* bacterial spores per gram of animal feed such as at least about $1\times10^4$ to $1\times10^5$ cfu of *Bacillus* bacterial spores per gram of animal feed, for example at least about $1\times10^5$ to $1\times10^6$ cfu of *Bacillus* bacterial spores per gram of animal feed, such as at least about $1\times10^6$ to $1\times10^7$ cfu of *Bacillus* bacterial spores per gram of animal feed, for example at least about $1\times10^7$ to $1\times10^8$ cfu of *Bacillus* bacterial spores per gram of animal feed, such as at least about $1\times10^8$ to $1\times10^9$ cfu of *Bacillus* bacterial spores per gram of animal feed, for example at least about $1\times10^9$ to $1\times10^{10}$ cfu of *Bacillus* bacterial spores per gram of animal feed or any combination of these intervals. The animal feed may comprise a probiotic composition or formulation including about $1\times10^4$, about $1\times10^5$, about $1\times10^6$, about $1\times10^7$, about $1\times10^8$, about $1\times10^9$ or about $1\times10^{10}$ cfu of *Bacillus* bacterial spores per gram of animal feed. In embodiments, the animal feed may comprise a probiotic composition or formulation including at least one *Bacillus* isolate or a combination of two or more *Bacillus* isolates.

In embodiments, an animal feed may comprise one or more of corn, soybean, rye, barley, wheat, oats, sorghum, distiller's dried grains with solubles (DDGS), or other ethanol byproduct, or any combination thereof. In embodiments, an animal feed may comprise one or more of corn, soybean, rye, barley, wheat, oats, and sorghum in various amounts. In further embodiments, an animal feed may, for example, comprise about 5%, about 6%, about 7%, about 8%, about 9%, about 10%, about 11%, about 12%, about 13%, about 14%, about 15%, about 16%, about 17%, about 18%, about 19% about 20%, about 25%, about 30%, about 35%, about 40%, about 45%, about 50%, about 55%, about 60%, about 65%, about 70%, about 75%, about 80%, about 85%, about 90%, about 95%, about 99% or about 100%, including all integers in between, of any one or more of corn, soybean, rye, barley, wheat, oats, sorghum, or DDGS. In some embodiments, the animal feed is bird feed.

In one embodiment the invention relates to a *Bacillus amyloliquefaciens* strain JD17 having the deposit accession number NRRL B-67142; a strain having all of the identifying characteristics of *Bacillus amyloliquefaciens* strain JD17 having the deposit accession number NRRL B-67142 or a mutant thereof.

In one embodiment the invention relates to a *Bacillus licheniformis* strain AM1002 having the deposit accession number NRRL B-67143; a strain having all of the identifying characteristics of *Bacillus licheniformis* strain AM1002 having the deposit accession number NRRL B-67143 or a mutant thereof.

In one embodiment the invention relates to a *Bacillus amyloliquefaciens* strain AM0938 having the deposit accession number NRRL B-67144; a strain having all of the identifying characteristics of *Bacillus amyloliquefaciens* strain AM0938 having the deposit accession number NRRL B-67144 or a mutant thereof.

In one embodiment the invention relates to a *Bacillus amyloliquefaciens* strain AM1109B having the deposit accession number NRRL B-67146; a strain having all of the identifying characteristics of *Bacillus amyloliquefaciens* strain AM1109B having the deposit accession number NRRL B-67146 or a mutant thereof.

In one embodiment the invention relates to a *Bacillus amyloliquefaciens* strain AM1101 having the deposit accession number NRRL B-67147; a strain having all of the identifying characteristics of *Bacillus amyloliquefaciens* strain AM1101 having the deposit accession number NRRL B-67147 or a mutant thereof.

In one embodiment the invention relates to a *Bacillus amyloliquefaciens* strain AM0939 having the deposit accession number NRRL B-67148; a strain having all of the identifying characteristics of *Bacillus amyloliquefaciens* strain AM0939 having the deposit accession number NRRL B-67148 or a mutant thereof.

In one embodiment the invention relates to a *Bacillus amyloliquefaciens* strain AM0934 having the deposit accession number NRRL B-67149; a strain having all of the identifying characteristics of *Bacillus amyloliquefaciens* strain AM0934 having the deposit accession number NRRL B-67149 or a mutant thereof.

In one embodiment the invention relates to a *Bacillus amyloliquefaciens* strain AM0940 having the deposit accession number NRRL B-67278; a strain having all of the identifying characteristics of *Bacillus amyloliquefaciens* strain AM0940 having the deposit accession number NRRL B-67278 or a mutant thereof.

In one embodiment the invention relates to a *Bacillus amyloliquefaciens* strain AM0933 having the deposit accession number NRRL B-67277; a strain having all of the identifying characteristics of *Bacillus amyloliquefaciens* strain AM0933 having the deposit accession number NRRL B-67277 or a mutant thereof.

V. Methods of Use

Various aspects relate to methods for improving, enhancing and/or facilitating digestion of nutrients in animals. In further aspects, methods of increasing body weight, increasing bone strength and improving bone composition (for example, mineral content) in an animal are provided. Methods for decreasing or reducing feed conversion ratio, intestinal viscosity of feed in the gastrointestinal tract, and bacterial translocation in an animal are provided. Methods for maintaining or reducing feed intake in an animal are provided.

In various aspects, a probiotic composition or formulation as described herein is provided to an animal to improve, enhance and/or facilitate digestibility, availability and/or absorption of nutrients in animal feed. In various embodiments, a probiotic composition or formulation includes at least one enzyme producing bacterial isolate. In embodiments, one or more, two or more or three or more isolates may be a *Bacillus*, for example any of a *Bacillus subtilis, Bacillus amyloliquefaciens*, or any combination thereof. In embodiments, a probiotic composition or formulation a probiotic composition for improving digestion of nutrients in an animal includes at least two enzyme producing *Bacillus* isolates selected from *Bacillus amyloliquefaciens* JD17 (NRRL Deposit B-67142), *Bacillus licheniformis* AM1002 (NRRL Deposit B-67143), *Bacillus amyloliquefaciens* AM0938 (NRRL Deposit B-67144), *Bacillus amyloliquefaciens* AM1109B (NRRL Deposit B-67146), *Bacillus amyloliquefaciens* AM1101 (NRRL Deposit B-67147), *Bacillus amyloliquefaciens* AM0939 (NRRL Deposit B-67148), *Bacillus amyloliquefaciens* AM0934 (NRRL Deposit B-67149), *Bacillus amyloliquefaciens* AM0933 (NRRL Deposit B-67277), *Bacillus amyloliquefaciens* AM0940 (NRRL Deposit B-67278), or any combination thereof. In embodiments the *Bacillus* isolates are selected from *Bacillus licheniformis* AM1002 (NRRL Deposit B-67143), *Bacillus amyloliquefaciens* AM0938 (NRRL Deposit B-67144). In embodiments, each of *Bacillus licheniformis* AM1002 (NRRL Deposit B-67143), *Bacillus amyloliquefaciens* AM0938 (NRRL Deposit B-67144) is selected. In embodiments the *Bacillus* isolates are selected from *Bacillus licheniformis* AM1002 (NRRL Deposit B-67143), *Bacillus amyloliquefaciens* AM0938 (NRRL Deposit B-67144) and *Bacillus amyloliquefaciens* JD17 (NRRL Deposit B-67142). In embodiments, each of *Bacillus licheniformis* AM1002 (NRRL Deposit B-67143), *Bacillus amyloliquefaciens* AM0938 (NRRL Deposit B-67144) and *Bacillus amyloliquefaciens* JD17 (NRRL Deposit B-67142) is selected.

In various aspects, a method of improving digestibility and improved digestion of nutrients in an animal is provided. The improvements may reduce adverse gastrointestinal states that result from the presence of non-digestible nutrients. An adverse gastrointestinal state may be overgrowth of opportunistic pathogens or nonpathogenic bacteria, gut inflammation, leakage of bacteria across the gastrointestinal tract surface or barrier, low body weight gain resulting from low absorption of nutrients, and chronic to severe flushing (for example, diarrhea). In embodiments, the method includes administering a probiotic composition or formulation set forth herein to an animal. The composition or formulation promotes breakdown of non-digestible nutrients and/or difficult to digest nutrients, and/or increasing digestion and/or absorption of nutrients. Non-digestible or difficult to digest nutrients include, for example, non-starch polysaccharides.

In various embodiments, a method of improving digestibility and improved digestion of nutrients in an animal corresponds to an increase and/or a decrease in one or more quantifiable parameters or indications. In embodiments, a quantifiable parameter or indication includes, but is not limited to, body weight, feed intake, feed conversion ratio, bone strength, bone composition, intestinal viscosity and bacterial translocation.

In embodiments, a probiotic composition or formulation, as disclosed herein, provided to an animal in animal feed increases the body weight of an animal compared to an animal provided a feed without a probiotic composition or formulation. In embodiments, an increase in body weight does not correspond to an increase in feed intake. For comparison purposes, the feed provided to an animal including a probiotic composition or formulation may be similar to the feed provided to an animal without a probiotic composition or formulation. In embodiments, the feed conversion ratio of an animal provided a feed including a probiotic composition or formulation, as disclosed herein, is decreased compared to the feed conversion ratio of an animal provided a feed without a probiotic composition or formulation.

In embodiments, a probiotic composition or formulation, as disclosed herein, provided to an animal in animal feed decreases intestinal viscosity compared to an animal provided a feed without a probiotic composition or formulation. In embodiments, a probiotic composition or formulation, as disclosed herein, provided to an animal in animal feed decreases bacterial translocation compared to an animal provided a feed without a probiotic composition or formulation.

In various aspects, methods of providing a probiotic composition or formulation in an animal feed are provided. In embodiments, an animal feed may comprise one or more of corn, soybean, rye, barley, wheat, oats, sorghum, distiller's dried grains with solubles (DDGS), or other ethanol byproduct, or any combination thereof. In embodiments, an animal feed may comprise one or more of corn, soybean, rye, barley, wheat, oats, and sorghum in various amounts. In further embodiments, an animal feed may, for example, comprise about 5%, about 6%, about 7%, about 8%, about 9%, about 10%, about 11%, about 12%, about 13%, about 14%, about 15%, about 16%, about 17%, about 18%, about 19% about 20%, about 25%, about 30%, about 35%, about 40%, about 45%, about 50%, about 55%, about 60%, about 65%, about 70%, about 75%, about 80%, about 85%, about 90%, about 95%, about 99% or about 100%, including all integers in between, of any one or more of corn, soybean, rye, barley, wheat, oats, sorghum, or DDGS.

In various aspects, methods of including a probiotic composition or formulation in an animal feed are provided. In embodiments, the animal feed may comprise a probiotic composition or formulation including about $1 \times 10^4$ to $1 \times 10^{10}$ cfu of bacterial spores per gram of animal feed such as at least about $1 \times 10^4$ to $1 \times 10^5$ cfu of spores per gram of animal feed, for example at least about $1 \times 10^5$ to $1 \times 10^6$ cfu of spores per gram of animal feed, such as at least about $1 \times 10^6$ to $1 \times 10^7$ cfu of spores per gram of animal feed, for example at least about $1 \times 10^7$ to $1 \times 10^8$ cfu of spores per gram of animal feed, such as at least about $1 \times 10^8$ to $1 \times 10^9$ cfu of spores per gram of animal feed, for example at least about $1 \times 10^9$ to $1 \times 10^{10}$ cfu of spores per gram of animal feed or any combination of these intervals. In further embodiments, the animal feed may comprise a probiotic composition or formulation including about $1 \times 10^4$, about $1 \times 10^5$, about $1 \times 10^6$, about $1 \times 10^7$, about $1 \times 10^8$, about $1 \times 10^9$ or about $1 \times 10^{10}$ cfu of bacterial spores per gram of animal feed. In embodiments, the animal feed may comprise at least one bacterial isolate or may comprise a combination of two or more bacterial isolates as disclosed herein. In embodiments, a probiotic composition or formulation is included in bird feed. In some embodiments, the bird feed is chicken feed.

In various embodiments, a bacterial isolate may be included in an animal feed as the number of bacteria spores per gram of feed. In embodiments, a bacterial isolate may be included in an animal feed at least about $1 \times 10^4$ to $1 \times 10^{10}$ spores per gram of animal feed such as at least about $1 \times 10^4$ to $1 \times 10^5$ spores per gram of animal feed, for example at least about $1 \times 10^5$ to $1 \times 10^6$ spores per gram of animal feed, such as at least about $1 \times 10^6$ to $1 \times 10^7$ spores per gram of animal feed, for example at least about $1 \times 10^7$ to $1 \times 10^8$ spores per gram of animal feed, such as at least about $1 \times 10^8$ to $1 \times 10^9$ spores per gram of animal feed, for example at least about $1 \times 10^9$ to $1 \times 10^{10}$ spores per gram of animal feed or any combination of these intervals. In embodiments, a bacterial isolate may be included in an animal feed at least about $1 \times 10^4$, $1 \times 10^5$, $1 \times 10^6$, $1 \times 10^7$, $1 \times 10^8$, $1 \times 10^9$, or $1 \times 10^{10}$ spores per gram of animal feed. In embodiments, a bacterial isolate is *Bacillus*. In embodiments, a bacterial isolate is included in bird feed. In some embodiments, the bird feed is chicken feed.

In various aspects, an animal may be a bird. In embodiments, a bird may include a neonatal bird or an adult bird. In embodiments, a bird may be poultry, including, but not limited to, a chicken, a turkey, a duck, a goose, or a pheasant.

VI. Selection Methods

Various aspects relate to methods of selecting one or more bacterial isolates having enzyme activity. In aspects, methods of screening bacterial isolates for enzyme activity are provided.

In various embodiments, a bacterial isolate may be screened for enzyme production activity by screening for presence of one or more enzymes produced. In embodiments, the bacterial isolate is capable of producing at least one enzyme. In embodiments, the bacterial isolate produces at least one of phytase, protease, lipase, cellulase, xylanase, or enzymes or materials with the foregoing activity, or any combination thereof. A bacterial isolate may be further screened for the ability of the bacterial isolate to produce a biofilm. A bacterial isolate may also be screened for the ability of the bacterial isolate to sporulate or produce spores. A bacterial isolate may further be screened and selected as one capable of improving one or more parameters or indications.

In embodiments, a *Bacillus* isolate produces at least about $1\times10^4$ to $1\times10^{10}$ spores per gram (or ml) of fermentate, such as at least about $1\times10^4$ to $1\times10^5$ spores per gram (or ml) of fermentate, for example at least about $1\times10^5$ to $1\times10^6$ spores per gram (or ml) of fermentate, such as at least about $1\times10^6$ to $1\times10^7$ spores per gram (or ml) of fermentate, for example at least about $1\times10^7$ to $1\times10^8$ spores per gram (or ml) of fermentate, such as at least about $1\times10^8$ to $1\times10^9$ spores per gram (or ml) of fermentate, for example at least about $1\times10^9$ to $1\times10^{10}$ spores per gram (or ml) of fermentate or any combination of these intervals. In embodiments, the *Bacillus* isolate produces at least about $1\times10^4$, $1\times10^5$, $1\times10^6$, $1\times10^7$, $1\times10^8$, $1\times10^9$, or $1\times10^{10}$ spores per gram of (or ml) of fermentate. In embodiments, the *Bacillus* isolate produces spores under controlled conditions. In embodiments, the spores are resistant to treatment with high temperatures, for example, during animal feed processing and manufacture, for example those temperatures found in the pelleting process.

In embodiments, a *Bacillus* isolate may produce one or more enzymes having higher enzymatic activity against at least one macromolecule nutrient and one or more enzymes having lower enzymatic activity against at least one macromolecule nutrient, or a combination thereof. The activity of an enzyme may be measured using agar plates containing a macromolecule nutrient as a substrate and the growth of a bacterial isolate and area or zone of clearance determined. In embodiments, for example, phytase production may be measured using sodium phytate (Na-phytate), protease production may be measured using milk agar, lipase production may be measured using Spirit blue agar, cellulase production may be measured using carboxymethyl cellulose (CMC) Congo red agar, and xylanase production may be measured using beechwood xylan agar. In embodiments, quantitative enzyme activity may be measured as the quantity of active enzyme present under certain conditions, for example, the rate of reaction of an enzyme in the presence of a substrate per the reaction volume (expressed as moles of substrate converted per unit time). The specific activity of an enzyme may be measured as the activity of an enzyme per milligram of total protein and expressed as $\mu mol\ min^{-1}\ mg^{-1}$. Quantitative enzyme activity may be measured using enzyme assays known to those of ordinary skill in the art. In embodiments, an enzyme assay may be spectrophotometric assays, fluorometric assays, calorimetric assays, chemiluminescent assays, light scattering assays, microscale thermophoresis assays, radiometric assays, or chromatographic assays.

In various embodiments, a bacterial isolate may have suitable enzyme activity against a single macromolecule nutrient, or against several macromolecule nutrients. As described herein, a macromolecule nutrient may be non-starch polysaccharides (NSP; for example, fiber), phytate (for example, phytic acid), protein, lipids (for example, fats, including saturated and unsaturated fats), and carbohydrates (for example, polysaccharides). A *Bacillus* isolate may produce one or more enzymes capable of breaking down a non-starch polysaccharide, a phytate, a protein, a lipid, a carbohydrate, or any combination thereof.

The selection methods described herein are not limited to selecting only those bacteria with the highest enzymatic activity against a given macromolecule, but also include other factors as described herein.

In various embodiments, a bacterial isolate may be screened for the ability to germinate and develop full life cycle within various environments. In embodiments, the bacterial isolate may germinate and develop full life cycle in the gastrointestinal tract of an animal. In embodiments, the bacterial isolate may be screened using a gastroenteric model in vitro system as disclosed in Latorre et al. (2014, Poultry Science, 93(7): 1793-1800; the entire contents of which are hereby incorporated by reference) to simulate the environment within a gastrointestinal tract.

In various embodiments, a bacterial isolate may be screened for the ability of the bacterial isolate to increase the body weight or body weight gain of an animal. In embodiments, one or more bacterial isolates may be provided as a formulation in animal feed. Without being bound to theory, body weight or body weight gain may increase as a result of the gastrointestinal tract (GIT) working more optimally or efficiently, more nutrients are made available to the animal, and/or the feed conversion ratio increases. An animal provided a feed including a probiotic composition or formulation with one or more bacterial isolates may demonstrate an increase in body weight or body weight gain compared to the body weight or body weight gain of an animal provided a feed without a probiotic composition or formulation.

In various embodiments, a bacterial isolate may be screened for the ability to reduce or decrease the feed conversion ratio of an animal. In embodiments, the feed conversion ratio of an animal provided a feed including a probiotic composition or formulation with one or more bacterial isolates may decrease compared to the feed conversion ratio of an animal provided a feed without a probiotic composition or formulation. In embodiments, feed conversion ration may be measured as feed intake over body weight gain. In embodiments, the conversion of feed intake to an increase in body weight gain is decreased or improved in an animal provided a feed including a probiotic formulation compared to that of an animal provided feed without a probiotic formulation. In embodiments, feed consumed by an animal may be used more efficiently when a probiotic formulation of the present disclosure is included. Without being bound to theory, the animal may be able to absorb nutrients more effectively due to a change in the absorptive capacity of the animal and/or the availability of more nutrients in the gastrointestinal tract of an animal. An improvement, for example, measured as a decrease in the feed conversion ratio may be attributed to improved absorption of nutrients by the animal.

In various embodiments, a bacterial isolate may be screened for the ability of the bacterial isolate to reduce viscosity in the gastrointestinal tract (GIT) of an animal. Viscosity may be measured by determining the viscosity of the intestinal content of an animal provided a feed including a probiotic composition or formulation as described herein and comparing the viscosity to the intestinal viscosity of an animal provided a feed without a probiotic composition or formulation. Intestinal viscosity, digesta viscosity or viscosity may be measured as centipoise (cP; for example, 1 $cP=10^{-2}\ P=10^{-3}\ Pa\cdot s=1\ mPa\cdot s$; P is Poise, Pa·s is pascal second, mPa·s is mili pascal second). Viscosity may be measured using methods known to those of ordinary skill in the art, for example, a cone/plate viscometer. Intestinal or digesta viscosity may be increased in the presence of a non-digestible nutrient, for example non-starch polysaccharide, in animal feed. Without being bound to theory, an increase in intestinal viscosity may effect nutrient absorption in the GIT of an animal and reduce the amount of nutrients available for absorption. A decrease or reduction in intestinal or digesta viscosity in an animal provided by a probiotic composition or formulation as disclosed herein may increase the digestibility and availability of nutrients (for example, non-starch polysaccharide) to the animal. An increase in the availability and absorption of nutrients may correlate with an improvement in one or more parameters or indications.

In various embodiments, a bacterial isolate may be screened for the ability to reduce bacterial translocation in an animal. Bacterial translocation may be measured by detecting the presence of bacteria in the liver of an animal provided a feed including a probiotic composition or formulation as described herein and comparing to the presence of bacteria in the liver of an animal provided a feed without a probiotic composition or formulation. The presence of bacteria not ordinarily detected within healthy liver tissue, for example, *Escherichia coli* and *Enterococcus* species may be determined. Bacterial translocation may be measured as the number of cfu of bacteria (for example, *Escherichia coli*) detected in a sample of liver tissue. The number of cfu's may be expressed as cfu $Log_{10}$) per gram of liver tissue. Without being bound to theory, inflammation or physical damage to the intestine may result in defects in the intestinal barrier allowing bacteria present in the gastrointestinal tract to "leak" into the blood and internal organs. The presence of non-digestible feed nutrients, for example non-starch polysaccharides, can lead to overgrowth of opportunistic bacteria which may cause inflammation in the gastrointestinal tract of an animal. An increase in bacterial translocation may be an indication of reduced or impaired intestinal barrier function.

In various embodiments, a bacterial isolate may be screened for the ability of the bacterial isolate to increase bone strength and/or bone composition in an animal. An increase in bone strength may be measured by testing the breaking strength of a bone, for example, a tibia, using a tensile strength test system (Instron 4502 tensile strength test system, Instron, Norwood, Mass.). Bone strength may be measured as tibia strength load at yield in $kg/mm^2$. The bone strength of an animal provided a feed including a probiotic composition or formulation may be compared to the bone strength of an animal provided a feed without a probiotic composition or formulation. An increase in bone strength may be associated with an increase in the availability, absorption and utilization of vitamins and minerals contained in animal feed. Bone composition may be tested by burning one or more bones (for example, a tibia) from an animal and determining the total percent of ash. The ash may be analyzed to determine the mineral components or content of the bone, for example, the percent of calcium and percent of phosphorus in the bone ash may be measured. The bone composition of an animal provided a feed including a probiotic composition or formulation may be compared to the bone composition of an animal provided a feed without a probiotic composition or formulation. An increase in bone composition or content may be indicative of improved bone mineralization.

VII. Probiotic Formulation in Animal Feed

In various aspects, the formulation of probiotic compositions and their subsequent inclusion in an animal feed is believed to be within the skill of those in the art.

In various embodiments, the probiotic formulations may be included in animal feed formulated as a dry powder, suspension or solution. The animal feed may comprise a probiotic formulation including about $1 \times 10^4$ to about $1 \times 10^{10}$ cfu of bacterial spores per gram of animal feed, such as about $1 \times 10^4$ to about $1 \times 10^5$ cfu of bacterial spores per gram of animal feed, for example about $1 \times 10^5$ to about $1 \times 10^6$ cfu of bacterial spores per gram of animal feed, such as about $1 \times 10^6$ to about $1 \times 10^7$ cfu of bacterial spores per gram of animal feed, for example about $1 \times 10^7$ to about $1 \times 10^8$ cfu of bacterial spores per gram of animal feed, such as about $1 \times 10^8$ to about $1 \times 10^9$ cfu of bacterial spores per gram of animal feed, for example about $1 \times 10^9$ to about $1 \times 10^{10}$ cfu of bacterial spores per gram of animal feed, or any combination of these intervals. The animal feed may comprise a probiotic formulation including about $1 \times 10^4$, about $1 \times 10^5$, about $1 \times 10^6$, about $1 \times 10^7$, about $1 \times 10^8$, about $1 \times 10^9$ or about $1 \times 10^{10}$ cfu of bacterial spores per gram of animal feed. The animal feed may comprise a probiotic formulation including at least one bacterial isolate or a combination of two or more bacterial isolates.

In various embodiments, a bacterial isolate may be included in an animal feed as the number of bacteria spores per gram of feed. In embodiments, a bacterial isolate may be included in an animal feed at least about $1 \times 10^4$ to about $1 \times 10^{10}$ spores per gram of animal feed, such as at least about $1 \times 10^4$ to $1 \times 10^5$ spores per gram of animal feed, for example at least about $1 \times 10^5$ to $1 \times 10^6$ spores per gram of animal feed, such as at least about $1 \times 10^6$ to $1 \times 10^7$ spores per gram of animal feed, for example at least about $1 \times 10^7$ to $1 \times 10^8$ spores per gram of animal feed, such as at least about $1 \times 10^8$ to $1 \times 10^9$ spores per gram of animal feed, for example at least about $1 \times 10^9$ to $1 \times 10^{10}$ spores per gram of animal feed or any combination of these intervals. In embodiments, a bacterial isolate may be included in an animal feed at least about $1 \times 10^4$, about $1 \times 10^5$, about $1 \times 10^6$, about $1 \times 10^7$, about $1 \times 10^8$, about $1 \times 10^9$, or about $1 \times 10^{10}$ spores per gram of animal feed. In embodiments one or more bacterial isolates may be included in animal feed. In some embodiments, a bacterial isolate is *Bacillus*. In embodiments, a bacterial isolate may be included in bird feed. In some embodiments, bird feed is chicken feed.

In various embodiments, the probiotic formulations may include at least one a probiotic composition for improving digestion of nutrients in an animal includes at least two enzyme producing *Bacillus* isolates selected from *Bacillus amyloliquefaciens* JD17 (NRRL Deposit B-67142), *Bacillus licheniformis* AM1002 (NRRL Deposit B-67143), *Bacillus amyloliquefaciens* AM0938 (NRRL Deposit B-67144), *Bacillus amyloliquefaciens* AM1109B (NRRL Deposit B-67146), *Bacillus amyloliquefaciens* AM1101 (NRRL Deposit B-67147), *Bacillus amyloliquefaciens* AM0939 (NRRL Deposit B-67148), *Bacillus amyloliquefaciens* AM0934 (NRRL Deposit B-67149), *Bacillus amyloliquefaciens* AM0933 (NRRL Deposit B-67277), *Bacillus amyloliquefaciens* AM0940 (NRRL Deposit B-67278), or any combination thereof.

In various embodiments, a probiotic formulation is included in animal feed before, during or after the pelleting stage of the feed process. The probiotic formulations include one or more *Bacillus* isolates capable of retaining enzyme activity after exposure to various conditions. In embodiments, the *Bacillus* isolates retain enzyme activity after exposure to the conditions used during the feed process. In embodiments, the *Bacillus* isolates retain enzyme activity after exposure to high temperatures used during and after the pelleting stage of the feed process. In embodiments, the probiotic formulation as disclosed herein is included at the pelleting stage of the feed process. Probiotic formulation as disclosed herein may be specifically included in a bird feed.

While the present disclosure has been described with specificity in accordance with certain of its embodiments, the following examples serve only to illustrate the disclosure and are not intended to limit the same. Each of the references, patents, patent applications, and the like recited in the present application are hereby incorporated by reference in its entirety.

Preferred Embodiments

Preferred embodiments of the invention are described in the set of items herein below.

1. A probiotic composition for improving digestion of nutrients in an animal comprising:
at least two enzyme producing *Bacillus* isolates selected from
*Bacillus amyloliquefaciens* JD17 (NRRL Deposit B-67142),
*Bacillus licheniformis* AM1002 (NRRL Deposit B-67143),
*Bacillus amyloliquefaciens* AM0938 (NRRL Deposit B-67144),
*Bacillus amyloliquefaciens* AM1109B (NRRL Deposit B-67146),
*Bacillus amyloliquefaciens* AM1101 (NRRL Deposit B-67147),
*Bacillus amyloliquefaciens* AM0939 (NRRL Deposit B-67148),
*Bacillus amyloliquefaciens* AM0934 (NRRL Deposit B-67149),
*Bacillus amyloliquefaciens* AM0933 (NRRL Deposit B-67277), and
*Bacillus amyloliquefaciens* AM0940 (NRRL Deposit B-67278),
or any combination thereof, and an agriculturally acceptable excipient.

2. The probiotic composition of item 1, wherein the at least two enzyme producing *Bacillus* isolates produce phytase, protease, lipase, cellulase, and xylanase.

3. The probiotic composition of item 1, wherein the at least two enzyme producing *Bacillus* isolates each individually produce phytase, protease, lipase, cellulase, and xylanase.

4. The probiotic composition of any of items 1-3, wherein the at least two enzyme producing *Bacillus* isolates form a biofilm.

5. The probiotic composition of any of items 1-4, wherein the at least two enzyme producing *Bacillus* isolates are spore forming *Bacillus*.

6. The probiotic composition of item 5, wherein the spore forming *Bacillus* produces at least about $1 \times 10^4$ to about $1 \times 10^{11}$ spores per gram of bacteria.

7. The probiotic composition of any of items 1-6, wherein the probiotic composition is provided in an animal feed.

8. The probiotic composition of item 7, wherein the probiotic composition is included in the animal feed during pelleting.

9. The probiotic composition of item 7, wherein the animal feed is bird feed.

10. The probiotic composition of item 9, wherein the bird feed comprises corn, soybean, rye, barley, wheat, oats, sorghum, distiller's dried grains with solubles, or any combination thereof.

11. The probiotic composition of item 7, wherein the probiotic composition is included in the animal feed at $1 \times 10^4$ to $1 \times 10^{10}$ colony forming units per gram of feed.

12. The probiotic composition of any of items 1-11, wherein the improved digestion of nutrients corresponds to an increase in one or more parameters or indications.

13. The probiotic composition of item 12, wherein the one or more parameters or indications is body weight, bone strength and/or bone composition.

14. The probiotic composition of item 13, wherein the bone composition is measured as total ash, calcium content and phosphorus content.

15. A probiotic formulation for improving digestion of nutrients in an animal comprising:
at least two enzyme producing *Bacillus* isolates selected from
*Bacillus amyloliquefaciens* JD17 (NRRL Deposit B-67142),
*Bacillus licheniformis* AM1002 (NRRL Deposit B-67143),
*Bacillus amyloliquefaciens* AM0938 (NRRL Deposit B-67144),
*Bacillus amyloliquefaciens* AM1109B (NRRL Deposit B-67146),
*Bacillus amyloliquefaciens* AM1101 (NRRL Deposit B-67147),
*Bacillus amyloliquefaciens* AM0939 (NRRL Deposit B-67148),
*Bacillus amyloliquefaciens* AM0934 (NRRL Deposit B-67149),
*Bacillus amyloliquefaciens* AM0933 (NRRL Deposit B-67277), or
*Bacillus amyloliquefaciens* AM0940 (NRRL Deposit B-67278), or any combination thereof and an agriculturally acceptable excipient.

16. The probiotic formulation of item 15, wherein the at least two enzyme producing *Bacillus* isolates produce phytase, protease, lipase, cellulase, and xylanase.

17. The probiotic formulation of item 15, wherein the at least two enzyme producing *Bacillus* isolates each individually produce phytase, protease, lipase, cellulase, and xylanase.

18. The probiotic formulation of any of items 15-17, wherein the at least two enzyme producing *Bacillus* isolates form a biofilm.

19. The probiotic formulation of item 15, wherein the at least two enzyme producing *Bacillus* isolates are spore forming *Bacillus*.

20. The probiotic formulation of item 19, wherein the spore forming *Bacillus* produces at least about $1 \times 10^4$ to about $1 \times 10^{11}$ spores per gram of bacteria.

21. The probiotic formulation of any of items 15-20, wherein the probiotic formulation is provided in an animal feed.

22. The probiotic formulation of item 21, wherein the probiotic formulation is included in the animal feed during pelleting.

23. The probiotic formulation of item 21, wherein the animal feed is bird feed.

24. The probiotic formulation of item 23, wherein the bird feed comprises corn, soybean, rye, barley, wheat, oats, sorghum, distiller's dried grains with solubles, or any combination thereof.

25. The probiotic formulation of item 21, wherein the probiotic formulation is included in the animal feed at $1 \times 10^4$ to $1 \times 10^{10}$ colony forming units per gram of feed.

26. The probiotic formulation of any of items 15-25, wherein the improved digestion of nutrients corresponds to an increase in one or more parameters or indications.

27. The probiotic formulation of item 26, wherein the one or more parameters or indications is body weight, bone strength and bone composition.

28. The probiotic formulation of item 27, wherein the bone composition is measured as total ash, calcium content and phosphorus content.

29. An enzyme producing *Bacillus* bacterial isolate comprising:
a combination of two or more *Bacillus* bacterial isolates selected from
*Bacillus amyloliquefaciens* JD17 (NRRL Deposit B-67142),
*Bacillus licheniformis* AM1002 (NRRL Deposit B-67143),

*Bacillus amyloliquefaciens* AM0938 (NRRL Deposit B-67144),
*Bacillus amyloliquefaciens* AM1109B (NRRL Deposit B-67146),
*Bacillus amyloliquefaciens* AM1101 (NRRL Deposit B-67147),
*Bacillus amyloliquefaciens* AM0939 (NRRL Deposit B-67148),
*Bacillus amyloliquefaciens* AM0934 (NRRL Deposit B-67149),
*Bacillus amyloliquefaciens* AM0933 (NRRL Deposit B-67277), and
*Bacillus amyloliquefaciens* AM0940 (NRRL Deposit B-67278),
and an agriculturally acceptable excipient, wherein at least two enzyme producing *Bacillus* isolates produce phytase, protease, lipase, cellulose, and xylanase.

30. The enzyme producing *Bacillus* bacterial isolate of item 29, wherein the at least two enzyme producing *Bacillus* isolates each individually produce phytase, protease, lipase, cellulose, and xylanase.

31. The enzyme producing *Bacillus* bacterial isolate of item 29 or 30, wherein the enzyme producing *Bacillus* bacterial isolate improves digestion of nutrients in an animal.

32. The enzyme producing *Bacillus* bacterial isolate of any of items 29-31, wherein the improved digestion of nutrients corresponds to an increase in one or more parameters or indications.

33. The enzyme producing *Bacillus* bacterial isolate of item 32, wherein the one or more parameters or indications is body weight, bone strength and bone composition.

34. The enzyme producing *Bacillus* bacterial isolate of item 33, wherein the bone composition is measured as total ash, calcium content and phosphorus content.

35. A method for improving digestion of nutrients in an animal comprising:
providing a probiotic composition comprising at least two enzyme producing *Bacillus* bacterial isolates selected from
*Bacillus amyloliquefaciens* JD17 (NRRL Deposit B-67142),
*Bacillus licheniformis* AM1002 (NRRL Deposit B-67143),
*Bacillus amyloliquefaciens* AM0938 (NRRL Deposit B-67144),
*Bacillus amyloliquefaciens* AM1109B (NRRL Deposit B-67146),
*Bacillus amyloliquefaciens* AM1101 (NRRL Deposit B-67147),
*Bacillus amyloliquefaciens* AM0939 (NRRL Deposit B-67148),
*Bacillus amyloliquefaciens* AM0934 (NRRL Deposit B-67149),
*Bacillus amyloliquefaciens* AM0933 (NRRL Deposit B-67277), and
*Bacillus amyloliquefaciens* AM0940 (NRRL Deposit B-67278),
or any combination thereof, and an agriculturally acceptable excipient to the animal.

36. The method of item 35, wherein one or more parameters or indications are improved.

37. The method of item 36, wherein the one or more parameters or indications is body weight, feed intake, feed conversion ratio, bone strength, bone composition, viscosity, or bacterial translocation.

38. The method of any of items 35-37, wherein the probiotic composition is provided in an animal feed.

39. The method of item 38, wherein the animal feed comprises corn, soybean, rye, barley, wheat, oats, sorghum, distiller's dried grains with solubles or any combination thereof.

40. The method of any of items 35-39, wherein the at least two enzyme producing *Bacillus* bacterial isolates produce phytase, protease, lipase, cellulase, and xylanase.

41. The method item of any of items 35-39, wherein the at least two enzyme producing *Bacillus* bacterial isolates each individually produce phytase, protease, lipase, cellulase, and xylanase.

42. A method for improving digestion of nutrients in an animal comprising:
providing a probiotic formulation comprising at least one enzyme producing *Bacillus* selected from
*Bacillus amyloliquefaciens* JD17 (NRRL Deposit B-67142),
*Bacillus licheniformis* AM1002 (NRRL Deposit B-67143),
*Bacillus amyloliquefaciens* AM0938 (NRRL Deposit B-67144),
*Bacillus amyloliquefaciens* AM1109B (NRRL Deposit B-67146),
*Bacillus amyloliquefaciens* AM1101 (NRRL Deposit B-67147),
*Bacillus amyloliquefaciens* AM0939 (NRRL Deposit B-67148),
*Bacillus amyloliquefaciens* AM0934 (NRRL Deposit B-67149),
*Bacillus amyloliquefaciens* AM0933 (NRRL Deposit B-67277), and
*Bacillus amyloliquefaciens* AM0940 (NRRL Deposit B-67278), or any combination thereof, and
an agriculturally acceptable excipient to the animal.

43. The method of item 42, wherein one or more parameters or indications are improved.

44. The method of item 43, wherein the one or more parameters or indications is body weight, feed intake, feed conversion ratio, bone strength, bone composition, viscosity, or bacterial translocation.

45. The method of any of items 42-44, wherein the probiotic formulation is provided in an animal feed.

46. The method of item 45, wherein the animal feed comprises corn, soybean, rye, barley, wheat, oats, sorghum, distiller's dried grains with solubles or any combination thereof.

47. A method for selecting an enzyme producing bacterial isolate comprising:
a) identifying at least one bacterial isolate capable of producing one or more enzymes;
b) determining biofilm production in the at least one bacterial isolate selected from step a);
c) identifying the at least one bacterial isolate from step b) capable of forming spores; and
d) selecting the at least one bacterial isolate from step c) wherein said at least one bacterial isolate is capable of improving one or more parameters or indications.

48. The method of item 47, wherein the at least one bacterial isolate produces at least one enzyme wherein said enzyme is phytase, protease, lipase, cellulase, xylanase, or any combination thereof.

49. The method of item 47, wherein the at least one bacterial isolate is *Bacillus*.

50. The method of item 49, wherein the *Bacillus* is selected from
*Bacillus amyloliquefaciens* JD17 (NRRL Deposit B-67142),
*Bacillus licheniformis* AM1002 (NRRL Deposit B-67143),
*Bacillus amyloliquefaciens* AM0938 (NRRL Deposit B-67144),

*Bacillus amyloliquefaciens* AM1109B (NRRL Deposit B-67146),
*Bacillus amyloliquefaciens* AM1101 (NRRL Deposit B-67147),
*Bacillus amyloliquefaciens* AM0939 (NRRL Deposit B-67148),
*Bacillus amyloliquefaciens* AM0934 (NRRL Deposit B-67149),
*Bacillus amyloliquefaciens* AM0933 (NRRL Deposit B-67277), and
*Bacillus amyloliquefaciens* AM0940 (NRRL Deposit B-67278), or any combination thereof.

51. The method of item 47, wherein the one or more parameters or indications is body weight, feed intake, feed conversion ratio, bone strength, bone composition, viscosity, or bacterial translocation.

52. The method of item 51, wherein the body weight, bone strength and/or bone composition is increased.

53. The method of item 51, wherein the feed conversion ratio, viscosity and/or bacterial translocation is decreased.

54. The method of item 47, wherein the at least one bacterial isolate selected in step d) is formulated as a probiotic formulation.

55. The method of item 54, wherein the probiotic formulation is provided in an animal feed.

56. The method of item 55, wherein the animal feed is bird feed.

57. An animal feed for improving digestion of nutrients in an animal comprising:
a probiotic composition comprising at least two enzyme producing *Bacillus* selected from
*Bacillus amyloliquefaciens* JD17 (NRRL Deposit B-67142),
*Bacillus licheniformis* AM1002 (NRRL Deposit B-67143),
*Bacillus amyloliquefaciens* AM0938 (NRRL Deposit B-67144),
*Bacillus amyloliquefaciens* AM1109B (NRRL Deposit B-67146),
*Bacillus amyloliquefaciens* AM1101 (NRRL Deposit B-67147),
*Bacillus amyloliquefaciens* AM0939 (NRRL Deposit B-67148),
*Bacillus amyloliquefaciens* AM0934 (NRRL Deposit B-67149),
*Bacillus amyloliquefaciens* AM0933 (NRRL Deposit B-67277), and
*Bacillus amyloliquefaciens* AM0940 (NRRL Deposit B-67278),
or any combination thereof, and an agriculturally acceptable excipient, 58. A probiotic composition for improving digestion of nutrients in an animal comprising:
at least two enzyme producing *Bacillus* isolates selected from
*Bacillus amyloliquefaciens* JD17 (NRRL Deposit B-67142),
*Bacillus licheniformis* AM1002 (NRRL Deposit B-67143),
*Bacillus amyloliquefaciens* AM0938 (NRRL Deposit B-67144),
*Bacillus amyloliquefaciens* AM1109B (NRRL Deposit B-67146),
*Bacillus amyloliquefaciens* AM1101 (NRRL Deposit B-67147),
*Bacillus amyloliquefaciens* AM0939 (NRRL Deposit B-67148),
*Bacillus amyloliquefaciens* AM0934 (NRRL Deposit B-67149),
*Bacillus amyloliquefaciens* AM0933 (NRRL Deposit B-67277), and
*Bacillus amyloliquefaciens* AM0940 (NRRL Deposit B-67278), or any combination thereof, and
an agriculturally acceptable excipient, wherein at least one of said enzyme producing *Bacillus* isolates produces phytase, protease, lipase, cellulase, and xylanase.

59. An animal feed for improving digestion of nutrients in an animal comprising:
a probiotic formulation comprising at least two enzyme producing *Bacillus* isolates selected from
*Bacillus amyloliquefaciens* JD17 (NRRL Deposit B-67142),
*Bacillus licheniformis* AM1002 (NRRL Deposit B-67143),
*Bacillus amyloliquefaciens* AM0938 (NRRL Deposit B-67144),
*Bacillus amyloliquefaciens* AM1109B (NRRL Deposit B-67146),
*Bacillus amyloliquefaciens* AM1101 (NRRL Deposit B-67147),
*Bacillus amyloliquefaciens* AM0939 (NRRL Deposit B-67148),
*Bacillus amyloliquefaciens* AM0934 (NRRL Deposit B-67149),
*Bacillus amyloliquefaciens* AM0933 (NRRL Deposit B-67277), and
*Bacillus amyloliquefaciens* AM0940 (NRRL Deposit B-67278),
or any combination thereof, and an agriculturally acceptable excipient.

60. A probiotic formulation for improving digestion of nutrients in an animal comprising:
at least two enzyme producing *Bacillus* isolates selected from
*Bacillus amyloliquefaciens* JD17 (NRRL Deposit B-67142),
*Bacillus licheniformis* AM1002 (NRRL Deposit B-67143),
*Bacillus amyloliquefaciens* AM0938 (NRRL Deposit B-67144),
*Bacillus amyloliquefaciens* AM1109B (NRRL Deposit B-67146),
*Bacillus amyloliquefaciens* AM1101 (NRRL Deposit B-67147),
*Bacillus amyloliquefaciens* AM0939 (NRRL Deposit B-67148),
*Bacillus amyloliquefaciens* AM0934 (NRRL Deposit B-67149),
*Bacillus amyloliquefaciens* AM0933 (NRRL Deposit B-67277), and
*Bacillus amyloliquefaciens* AM0940 (NRRL Deposit B-67278), or any combination thereof, and
an agriculturally acceptable excipient, wherein at least two of said enzyme producing *Bacillus* isolates produce phytase, protease, lipase, cellulase, and xylanase.

61. The probiotic formulation of item 60, wherein at least two of said enzyme producing *Bacillus* isolates each individually produce phytase, protease, lipase, cellulase, and xylanase.

62. A method for selecting an enzyme producing bacterial isolate comprising:
a) identifying at least one bacterial isolate capable of producing one or more enzymes;
b) determining biofilm production in the at least one bacterial isolate selected from step a);
c) identifying the at least one bacterial isolate from step b) capable of forming spores; and
d) selecting the at least one bacterial isolate from step c) wherein said at least one bacterial isolate is capable of improving one or more parameters or indications, and wherein at least one bacterial isolate produces phytase, protease, lipase, cellulase, and xylanase.

63. A *Bacillus amyloliquefaciens* strain JD17 having the deposit accession number NRRL B-67142; a strain having all of the identifying characteristics of *Bacillus amyloliquefaciens* strain JD17 having the deposit accession number NRRL B-67142 or a mutant thereof.

64. A *Bacillus licheniformis* strain AM1002 having the deposit accession number NRRL B-67143; a strain having all of the identifying characteristics of *Bacillus licheniformis* strain AM1002 having the deposit accession number NRRL B-67143 or a mutant thereof.

65. A *Bacillus amyloliquefaciens* strain AM0938 having the deposit accession number NRRL B-67144; a strain having all of the identifying characteristics of *Bacillus amyloliquefaciens* strain AM0938 having the deposit accession number NRRL B-67144 or a mutant thereof.

66. A *Bacillus amyloliquefaciens* strain AM0940 having the deposit accession number NRRL B-67278; a strain having all of the identifying characteristics of *Bacillus amyloliquefaciens* strain AM0940 having the deposit accession number NRRL B-67278 or a mutant thereof.

67. A *Bacillus amyloliquefaciens* strain AM1109B having the deposit accession number NRRL B-67146; a strain having all of the identifying characteristics of *Bacillus amyloliquefaciens* strain AM1109B having the deposit accession number NRRL B-67146 or a mutant thereof.

68. A *Bacillus amyloliquefaciens* strain AM1101 having the deposit accession number NRRL B-67147; a strain having all of the identifying characteristics of *Bacillus amyloliquefaciens* strain AM1101 having the deposit accession number NRRL B-67147 or a mutant thereof.

69. A *Bacillus amyloliquefaciens* strain AM0939 having the deposit accession number NRRL B-67148; a strain having all of the identifying characteristics of *Bacillus amyloliquefaciens* strain AM0939 having the deposit accession number NRRL B-67148 or a mutant thereof.

70. A *Bacillus amyloliquefaciens* strain AM0934 having the deposit accession number NRRL B-67149; a strain having all of the identifying characteristics of *Bacillus amyloliquefaciens* strain AM0934 having the deposit accession number NRRL B-67149 or a mutant thereof.

71. A *Bacillus amyloliquefaciens* strain AM0933 having the deposit accession number NRRL B-67277; a strain having all of the identifying characteristics of *Bacillus amyloliquefaciens* strain AM0933 having the deposit accession number NRRL B-67277 or a mutant thereof.

VIII. Examples

Identification, Characterization and Deposit of the Biological Material

The following biological materials were deposited under the terms of the Budapest Treaty at deposited with Agricultural Research Service Culture Collection (NRRL), 1815 North University Street, Peoria, Ill. 61604, U.S.A., and given the following accession numbers:

Deposit of Biological Material

| Identification | Accession Number | Date of Deposit |
| --- | --- | --- |
| *Bacillus amyloliquefaciens* JD17 | NRRL Deposit B-67142 | Oct. 29, 2015 |
| *Bacillus licheniformis* AM1002 | NRRL Deposit B-67143 | Oct. 29, 2015 |
| *Bacillus amyloliquefaciens* AM0938 | NRRL Deposit B-67144 | Oct. 29, 2015 |
| *Bacillus amyloliquefaciens* AM1109B | NRRL Deposit B-67146 | Oct. 29, 2015 |
| *Bacillus amyloliquefaciens* AM1101 | NRRL Deposit B-67147 | Oct. 29, 2015 |
| *Bacillus amyloliquefaciens* AM0939 | NRRL Deposit B-67148 | Oct. 29, 2015 |
| *Bacillus amyloliquefaciens* AM0934 | NRRL Deposit B-67149 | Oct. 29, 2015 |
| *Bacillus amyloliquefaciens* AM0933 | NRRL Deposit B-67277 | Jun. 15, 2016 |
| *Bacillus amyloliquefaciens* AM0940 | NRRL Deposit B-67278 | Jun. 15, 2016 |

The strains have been deposited under conditions that assure that access to the culture will be available during the pendency of this patent application to one determined by foreign patent laws to be entitled thereto. The deposits represent a substantially pure culture of the deposited strain. The deposits are available as required by foreign patent laws in countries wherein counterparts of the subject application or its progeny are filed. However, it should be understood that the availability of a deposit does not constitute a license to practice the subject invention in derogation of patent rights granted by governmental action.

Description of the Biological Material

*Bacillus amyloliquifaciens* AM0938 (NRRL Deposit B-67144) was isolated from poultry in 2009 in the Washington County Ark., USA. This strain was specieated using 16s rDNA sequencing.

*Bacillus licheniformis* AM1002 (NRRL Deposit B-67143) was isolated from poultry in 2010 in the Washington County Ark., USA. This strain was specieated using 16s rDNA sequencing.

*Bacillus amyloliquifaciens* JD17 (NRRL Deposit B-67142) was isolated from poultry in 2012 in the Washington County Ark., USA. This strain was specieated using 16s rDNA sequencing.

*Bacillus amyloliquefaciens* AM0933 (NRRL Deposit B-67277) was isolated from poultry in 2009 in the Washington County Ark., USA. This strain was specieated using 16s rDNA sequencing.

*Bacillus amyloliquefaciens* AM1109B (NRRL Deposit B-67146) was isolated from poultry in 2011 in the Washington County Ark., USA. This strain was specieated using 16s rDNA sequencing.

*Bacillus amyloliquefaciens* AM1101 (NRRL Deposit B-67147) was isolated from poultry in 2011 in the Washington County Ark., USA. This strain was specieated using 16s rDNA sequencing.

*Bacillus amyloliquefaciens* AM0939 (NRRL Deposit B-67148) was isolated from poultry in 2009 in the Washington County Ark., USA. This strain was specieated using 16s rDNA sequencing.

*Bacillus amyloliquefaciens* AM0934 (NRRL Deposit B-67149) was isolated from poultry in 2009 in the Washington County Ark., USA. This strain was specieated using 16s rDNA sequencing.

*Bacillus amyloliquefaciens* AM0940 (NRRL Deposit B-67278) was isolated from poultry in 2009 in the Washington County Ark., USA. This strain was specieated using 16s rDNA sequencing.

Example 1

Experiment 1: Selection Method

*Bacillus* isolates were evaluated as potential candidates for the production of different enzyme activities (e.g., the production of cellulase, protease, lipase, xylanase and phytase), biofilm synthesis, ability to reduce digesta viscosity, and germination/sporulation rate in an in vitro digestion model.

Thirty one (31) candidates were selected from a library of >1,000,000 pre-screened bacterial isolates. The bacterial candidates were incubated in tryptic soy broth (TSB; BD Difco Tryptic Soy Broth) media overnight at 37° C. The bacterial candidates were washed 3 times in saline by centrifugation at 2000 g for 15 minutes.

Bacterial candidates were screened for the production of lipase, cellulase, protease, phytase and xylanase enzyme activity. Bacterial candidates were plated on agar plates containing Spirit Blue Agar (incubated for 24 hours; lipase), carboxymethyl cellulose (CMC) Congo red agar (incubated for 48 hours; cellulase), milk agar (incubated for 24 hours; protease), Na-phytate agar (incubated for 120 hours; phytase), and beechwood xylan agar (incubated for 24 hours; xylanase). Bacterial growth and zone/area of clearance were determined (++++ indicated high activity, + indicated low activity).

Bacterial candidates were further screened for biofilm synthesis (Barbosa et al., 2005, *Applied and Environmental Microbiology* 71(2): 968-978; the entire contents of which are herein incorporated by reference). The bacterial candidates were incubated in TSB media overnight at 37° C. 10 µl samples were transferred to 0.5 ml casein-mannitol medium and incubated overnight at 37° C. The medium and rinsing water were discarded. The sample was stained with 1% w/v crystal violet and rinsed with water. The production of a biofilm ring was determined.

The 31 bacterial isolates screened were evaluated using various qualitative parameters (Table 1).

TABLE 1

Qualitative Evaluation Parameters for *Bacillus* Candidates as Enzyme Producers and Biofilm Synthesis.

| Number | Identification | Cellulase 48 h | Protease 24 h | Lipase 24 h | Xylanase 24 h | Phytase 120 h | Biofilm synthesis |
|---|---|---|---|---|---|---|---|
| 1 | NP122 (NRRL B-50910) | ++++ | +++ | ++ | + | ++ | ++ |
| 2 | JD17 | ++++ | +++ | ++ | +/− | ++ | + |
| 3 | AM1109A | +++ | + | ++++ | + | + | ++ |
| 4 | AM1109B | ++++ | + | ++++ | + | + | ++ |
| 5 | NP124 | ++ | ++ | +++ | − | + | + |
| 6 | AM0902 | +++ | + | + | +/− | +/− | + |
| 7 | B2 (NRRL B-50908) | ++ | ++ | +++ | ND | ND | + |
| 8 | RW41 | ++++ | ++ | ++ | + | ++ | + |
| 9 | B.L | + | + | ND | ND | ND | − |
| 10 | AM0904 (NRRL B-50914) | +++ | ++ | ++ | ND | ND | + |
| 11 | AM1010 | +++ | + | +++ | ND | ND | +/− |
| 12 | AM1101 | ++++ | ++ | +++ | − | ++ | ++ |
| 13 | AM1012 | ++ | ++ | ++ | ND | ND | + |
| 14 | AM1013 | ++ | ++ | ++ | ND | ND | + |
| 15 | AM0923 | ++++ | ++ | + | ND | ND | +/− |
| 16 | 19/49 | ++++ | ++ | ++ | ND | ND | + |
| 17 | AM0908 | ++ | ND | ND | ND | ND | + |
| 18 | AM0905 | ++ | +++ | +++ | + | +/− | ++ |
| 19 | AM0939 | ++++ | +++ | +++ | + | + | +/− |
| 20 | AM0940 | ++ | +++ | ++ | ND | ND | ++ |
| 21 | AM1002 | ++++ | ++++ | +++ | + | ++ | ++ |
| 22 | AM0933 | ++++ | ++ | ++ | ND | ND | ++ |
| 23 | AM0934 | +++ | ++++ | ++ | ND | ND | +/− |
| 24 | AM0938 | +++ | +++ | ++++ | + | ++ | +/− |
| 25 | AM0941 | + | + | ++ | ND | ND | ++ |
| 26 | NP117B | ND | ND | ND | +/− | + | + |
| 27 | NP121 | ND | ND | ND | + | +/− | + |
| 28 | MM65 | ND | ND | ND | + | ++ | ++ |
| 29 | NP001 | ND | ND | ND | + | + | + |
| 30 | NP002 | ND | ND | ND | − | + | + |
| 31 | NP126 | ND | ND | ND | − | + | + |

Three (3) bacterial isolate candidates were selected for further testing; *B. amyloliquefaciens* JD17 (isolate number 2), *B. licheniformis* AM1002 (isolate number 21), and *B. amyloliquefaciens* AM0938 (isolate number 24). These three bacterial candidates were further tested for the ability to sporulate.

Experiment 2: In Vitro Digestion Methodology Simulating the GIT of Poultry

Figure 2A:
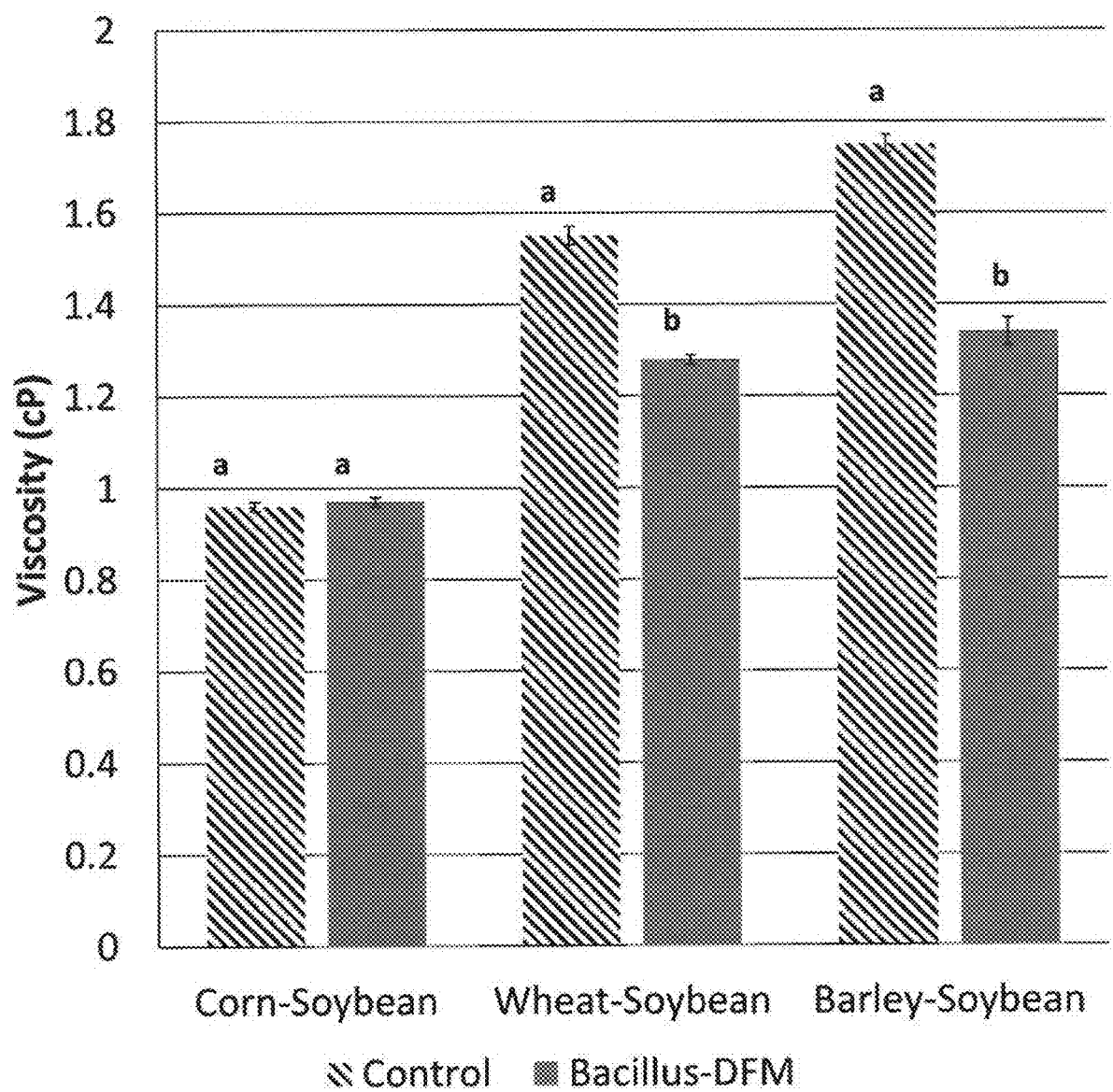
FIGS. 2A and 2B illustrate viscosity (cP) of various diets with and without *Bacillus* DFM-candidate.

The three bacterial candidates selected above (*B. amyloliquefaciens* isolate JD17 (NRRL Deposit B-67142), *B. licheniformiss* isolate AM1002 (NRRL Deposit B-67143), and *B. amyloliquefaciens* isolate AM0938 (NRRL Deposit B-67144) were combined, referred to herein as *Bacillus*-DFM candidate, and screened using an in vitro digestion methodology that simulates the GIT of poultry (FIG. 1). Different poultry feed diets were tested with and without the inclusion of the *Bacillus*-DFM candidate. The feed diets tested were corn-soybean, wheat-soybean, barley-soybean, rye-soybean and oats-soybean. Digesta viscosity and *Clostridium perfringens* proliferation were determined. Viscosity was measured after 3 hours and 15 minutes of in vitro digestion at 40° C. The mean data of 5 replicates per diet per treatment was calculated (FIG. 2A and FIG. 2B).

Figure 2B:
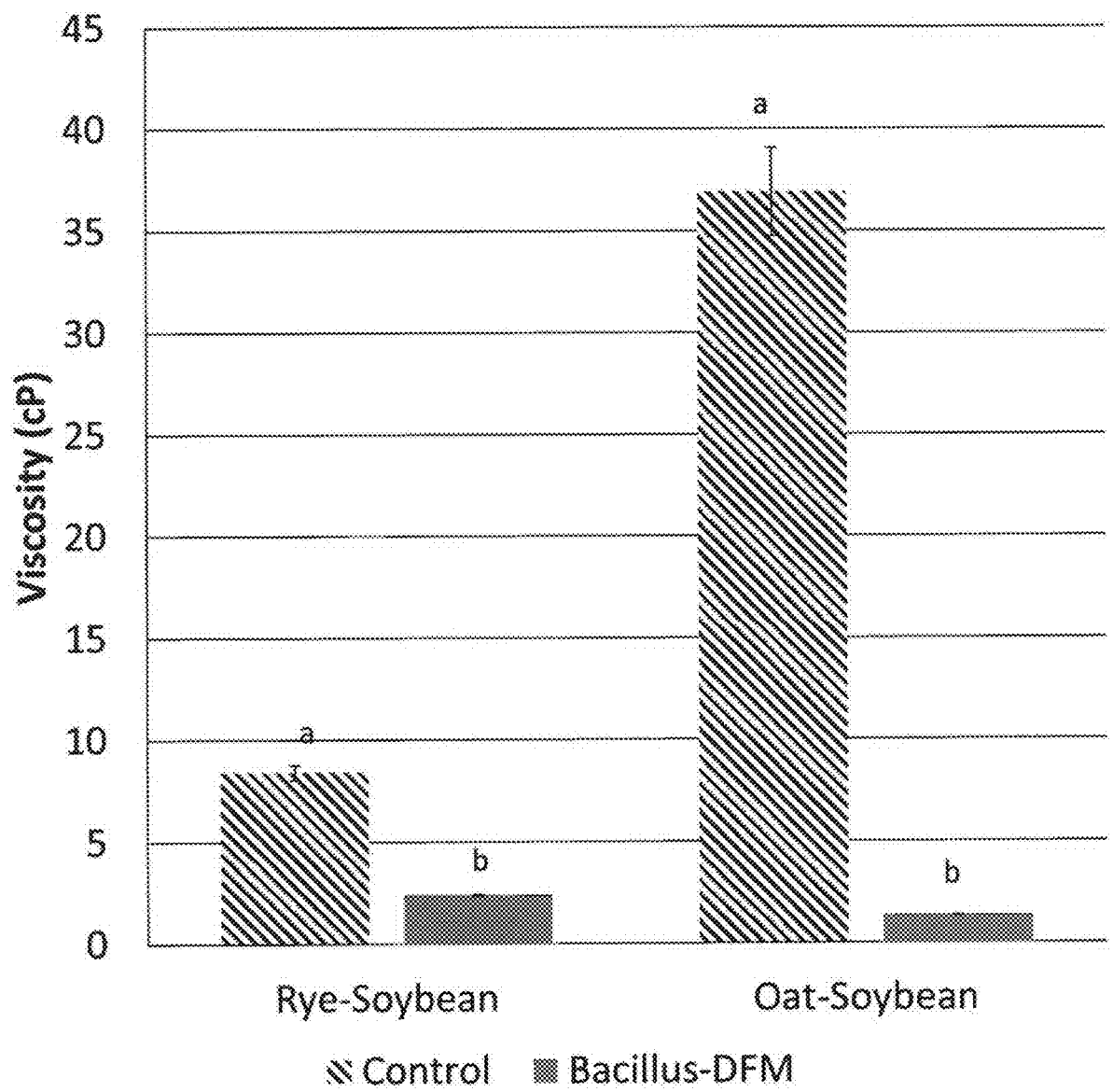

A statistically significant reduction in viscosity was demonstrated in the presence of *Bacillus*-DFM candidate in wheat-soybean, barley-soybean (FIG. 2A), rye-soybean and oats-soybean (FIG. 2B). No statistically significant reduction in viscosity was determined in the presence of *Bacillus*-DFM candidate in corn-soybean compared to the control (no *Bacillus*-DFM). Corn-soybean has a consistency similar to water and is the least viscous of the feeds tested. Without being bound to theory, the more viscous a feed the lower the diffusion of nutrients within the gastrointenstinal tract. Nutrients in a viscous feed have less contact with the intestinal wall and less nutrients are absorbed allowing more of them to travel into the small intestine. The greater amount of nutrients that travel to the small intestine and through to the ceca, the more bacteria can migrate to the small intestine leading to bacteriosis and can lead to necrotic enteritis. More nutrients pass through the bird reducing the amount of nutrients that are absorbed by the bird and reducing the nutritional value of the feed.

The *Bacillus*-DFM candidate was tested in vivo. Neonatal chickens were administered a feed with the *Bacillus*-DFM candidate (Group 2; n=25) and without *Bacillus*-DFM candidate (Group 1; n=25). The *Bacillus*-DFM candidate was provided in the feed at $1 \times 10^6$ spores per gram of feed. The neonatal chickens were fed a starter diet of rye-soybean from 0-10 days. At day 10, bacterial translocation (n=12), intestinal viscosity (n=5), bone strength and composition (n=12) were determined.

Bacterial translocation was determined by detecting the presence of *Escherichia coli* in the liver of the chickens. The right half of the liver from 12 chickens per group was weighed and homogenized. The liver samples were diluted 1:4 wt./vol. in saline. Tenfold serial dilutions were plated onto a MacConkey agar plate and bacterial growth was determined.

Viscosity was determined using the intestinal contents from the duodenum to cloaca of the chickens (Experiments 1 and 2; Table 2). The samples were centrifuged at 11000×g for 5 minutes. The supernatants were placed on ice until analysis. 0.5 ml of each sample was tested for viscosity at 40° C. using a cone/plate viscometer. Intestinal viscosity was determined from 5 chickens per group and expressed in centipoise (cP).

Bone parameters were determined by testing the breaking strength of the right tibia bone from a chicken using an Instron 4502 tensile strength test system. Bone composition was determined using the left tibia bone of a chicken. The tibia bone is burned and analyzed for the mineral composition by measuring the total percent of ash, percent of calcium and percent of phosphorus.

Statistical Analysis

Colony-forming data was converted to $\log_{10}$ cfu. Performance parameters, viscosity, bone parameters and cfu data were analyzed by Analysis of Variance (ANOVA) using the GLM procedure (SAS Institute Inc., Cary, N.C.) with statistical significance reported at $P < 0.05$.

TABLE 2

Evaluation of body weight, intestinal viscosity and liver bacterial translocation in broiler chickens (10 d of age).

| Diet | Body weight (g) | Intestinal viscosity (cP) | Bacterial translocation ($\log_{10}$ cfu) |
|---|---|---|---|
| Experiment 1 | | | |
| Rye-Soybean | $110.69 \pm 5.21^b$ | $500.6 \pm 71.80^a$ | $2.35 \pm 0.45^a$ |
| Rye-Soybean + DFM-Candidate | $137.67 \pm 4.94^a$ | $271.0 \pm 12.74^b$ | $0.98 \pm 0.27^b$ |
| Experiment 2 | | | |
| Rye-Soybean | $140.89 \pm 5.21^b$ | $591.4 \pm 51.72^a$ | $2.40 \pm 0.73^a$ |
| Rye-Soybean + DFM-Candidate | $167.66 \pm 6.94^a$ | $306.0 \pm 14.70^b$ | $1.12 \pm 0.55^b$ |

$^{a\text{-}b}$Superscripts within columns indicate significant difference at $p < 0.05$.

As shown in Table 2, the body weight of chickens fed a diet including *Bacillus*-DFM candidate was significantly higher than chickens fed a diet without *Bacillus*-DFM candidate. Intestinal viscosity was significantly reduced in chickens fed a diet including *Bacillus*-DFM candidate compared to chickens fed a diet without *Bacillus*-DFM candidate. The inclusion of the *Bacillus*-DFM candidate reduced the viscosity of the feed allowing more nutrients to be absorbed. The number of bacteria located in the liver was significantly reduced in chickens fed a diet including *Bacillus*-DFM candidate compared to chickens fed a diet without *Bacillus*-DFM candidate.

Bone strength and bone composition in neonatal broiler chickens fed with a Rye-based diet with or without *Bacillus*-DFM candidate was evaluated. Tibias were collected from 12 chickens per group and breaking strength, total ash, calcium and phosphorus were determined. The data is expressed as mean±standard error (SE).

TABLE 3

Evaluation of bone strength and composition in broiler chickens (10 day of age).

| Diet | Breaking strength (load in kg) | Total ash (%) | Ca (%) | P (%) |
|---|---|---|---|---|
| Experiment 1 | | | | |
| Rye-Soybean | $1.58 \pm 0.01^b$ | $34.87 \pm 0.35^b$ | $18.48 \pm 0.27^b$ | $13.15 \pm 0.12^b$ |
| Rye-Soybean + DFM-Candidate | $2.68 \pm 0.01^a$ | $54.87 \pm 0.39^a$ | $36.48 \pm 0.87^a$ | $26.15 \pm 0.82^a$ |
| Experiment 2 | | | | |
| Rye-Soybean | $2.25 \pm 0.03^b$ | $30.87 \pm 0.75^b$ | $21.32 \pm 0.46^b$ | $15.67 \pm 0.29^b$ |
| Rye-Soybean + DFM-Candidate | $2.58 \pm 0.09^a$ | $56.57 \pm 0.45^a$ | $40.28 \pm 0.21^a$ | $29.75 \pm 0.10^a$ |

$^{a\text{-}b}$Superscripts within columns indicate significant difference at $p < 0.05$.

As shown in Table 3, the breaking strength of the tibia bone increased in chickens fed a diet including the *Bacillus*-DFM candidate. The total ash, calcium and phosphorus content of the tibia bones increased in chickens fed a diet including the *Bacillus*-DFM candidate.

Experiment 3

The *Bacillus*-DFM candidate was evaluated in a rye-soybean diet over a 28 day period. Group 1 (control) was fed a rye-based diet that included no spores in the feed (8 replicates of 20 chickens, n=160). Group 2 was provided $1\times10^6$ spores per gram of rye-based feed of the *Bacillus*-DFM candidate (8 replicates of 20 chickens, n=160). Chickens were provided a starter diet from days 0 to 7 and a grower rye-soybean diet from days 8 to 28. The body weight (BW), feed intake (FI) and feed conversion ratio (FCR) of the chickens was measured weekly.

TABLE 4

Evaluation of body weight, feed intake and feed conversion ratio in broiler chickens.

| Parameters | Rye-based | Rye-based + DFM-Candidate |
|---|---|---|
| Starter (0-7 d) | | |
| BW (g) | 95.90 ± 3.21$^a$ | 101.93 ± 3.12$^a$ |
| FI (g) | 118.05 ± 2.78$^a$ | 116.33 ± 2.29$^a$ |
| FCR | 1.23 ± 0.03$^a$ | 1.15 ± 0.02$^{a*}$ |
| Grower (8-28 d) | | |
| BW (g) | 708.25 ± 6.22$^b$ | 728.20 ± 6.18$^a$ |
| FI (g) | 1701.62 ± 17.13$^a$ | 1694.10 ± 16.77$^a$ |
| FCR | 2.40 ± 0.02$^a$ | 2.33 ± 0.02$^b$ |
| Overall (0-28 d) | | |
| BW (g) | 804.13 ± 7.30$^b$ | 830.13 ± 6.43$^a$ |
| FI (g) | 1820.02 ± 17.83$^a$ | 1810.44 ± 17.03$^a$ |
| FCR | 2.26 ± 0.03$^a$ | 2.18 ± 0.02$^b$ |

$^{a-b}$Superscripts within columns indicate significant difference at P < 0.05.
$^a$*indicates a significant difference at (P = 0.06).

As shown in Table 4, the overall body weight of chickens fed a diet including *Bacillus*-DFM candidate was significantly higher than chickens fed a diet without *Bacillus*-DFM candidate. The feed intake value in chickens fed a diet including *Bacillus*-DFM candidate was not statistically different to the feed intake value of chickens fed a diet without *Bacillus*-DFM candidate. The increase in body weight in the chickens fed a diet with *Bacillus*-DFM candidate did not correlate with an increase in feed intake. The feed conversion ratio was significantly lower in chickens fed a diet including *Bacillus*-DFM candidate than chickens fed a diet without *Bacillus*-DFM candidate. The feed conversion ratio is a measure of the lbs of feed divided by the weight of the bird. An average amount is 1.5 lbs of feed is equivalent to 1 lb of meat on a bird. A decrease in the feed conversion ratio leads to a decrease in the amount of feed required to produce the same amount of meat.

At day 28 bacterial translocation, and intestinal viscosity of the intestinal contents from the duodenum to Meckel's diverticulum (measured as centipoise cP) in 8 chickens per group were measured. Bone strength and bone composition (total ash, calcium and phosphorus) were measured in the tibias of 8 chickens per group. Data is expressed as mean±SE.

TABLE 5

Evaluation of intestinal viscosity, bacterial translocation and bone composition in 28 day old broiler chickens.

| Diet | Rye-Soybean | Rye-Soybean + DFM-Candidate |
|---|---|---|
| Intestinal viscosity (cP) | 96.16 ± 2.95$^a$ | 61.52 ± 2.34$^b$ |
| Bacterial translocation (Log$_{10}$ cfu) | 1.45 ± 0.18$^a$ | 0.87 ± 0.15$^b$ |
| Breaking strength (load in kg) | 22.15 ± 0.93$^b$ | 26.51 ± 1.68$^a$ |
| Total ash (%) | 44.87 ± 0.95$^b$ | 55.01 ± 0.61$^a$ |
| Ca (%) | 18.48 ± 0.27$^b$ | 29.48 ± 0.27$^a$ |
| P (%) | 9.15 ± 0.12$^b$ | 15.15 ± 0.13$^a$ |

$^{a-b}$Superscripts within columns indicate significant difference at p < 0.05.

As shown in Table 5, intestinal viscosity and bacterial translocation was significantly decreased in chickens fed a diet including *Bacillus*-DFM candidate compared to chickens fed a diet without *Bacillus*-DFM candidate. The breaking strength of the tibia bones of chickens fed a diet with *Bacillus*-DFM candidate was significantly higher than chickens fed a diet without *Bacillus*-DFM candidate. The bone composition, for example, total ash, % calcium and % phosphorus, of chickens fed a diet including *Bacillus*-DFM candidate was significantly higher than chickens fed a diet without *Bacillus*-DFM candidate.

Experiment 4

The *Bacillus*-DFM candidate was evaluated in a rye-soybean diet fed to turkey poults over a 10 day period. Group 1 (control) was fed a rye-based diet that included no spores in the feed (1 replicate of 25 turkey poults, n=25). Group 2 was provided $1\times10^6$ spores per gram of rye-based feed of the *Bacillus*-DFM candidate (1 replicates of 25 turkey poults, n=25). The body weight of 25 turkey poults was determined. The digesta intestinal viscosity (expressed in Log$_{10}$ in centipoise (cP=$\frac{1}{100}$ dyne s/cm$^2$)) and bacterial translocation (expressed in cfu Log$_{10}$/g of tissue) of 12 of the turkey poults was measured. The data are expressed as mean±SE.

TABLE 6

Evaluation of body weight, digesta viscosity, and bacterial translocation to the liver in neonatal turkey poults.

| Diet | Body weight (g) | Digesta viscosity (cP Log$_{10}$) | Bacterial translocation (cfu Log$_{10}$) |
|---|---|---|---|
| Experiment 1 | | | |
| Rye-Soybean | 65.91 ± 3.61$^b$ | 2.03 ± 0.31$^a$ | 3.03 ± 0.51$^a$ |
| Rye-Soybean + DFM-Candidate | 82.85 ± 4.23$^a$ | 1.54 ± 0.22$^b$ | 1.24 ± 0.51$^b$ |
| Experiment 2 | | | |
| Rye-Soybean | 74.47 ± 1.59$^b$ | 2.80 ± 0.45$^a$ | 2.13 ± 0.67$^a$ |
| Rye-Soybean + DFM-Candidate | 95.60 ± 2.17$^a$ | 1.62 ± 0.53$^b$ | 0.35 ± 0.40$^b$ |

$^{a-b}$Superscripts within columns indicate significant difference at p < 0.05.

As shown in Table 6, the body weight significantly increased in turkeys fed a diet including *Bacillus*-DFM candidate compared to turkeys fed a diet without *Bacillus*-DFM candidate. The intestinal viscosity and bacterial translocation was significantly decreased in turkeys fed a diet including *Bacillus*-DFM candidate compared to turkeys fed a diet without *Bacillus*-DFM candidate.

The bone strength, bone diameter and bone composition of tibia bones from 12 turkey poults were collected and evaluated. Data is expressed as mean±SE.

TABLE 7

Evaluation of bone strength and bone composition in neonatal turkey poults.

| Diet | Tibia Strength (kg/mm$^2$) | Tibia Diameter (mm) | Total Ash (%) | Ca (%) | P (%) |
|---|---|---|---|---|---|
| Experiment 2 | | | | | |
| Rye-Soybean | 0.26 ± 0.02$^a$ | 4.45 ± 0.32$^a$ | 35.61 ± 0.81$^a$ | 27.35 ± 0.07$^a$ | 16.35 ± 0.52$^a$ |
| Rye-Soybean + DFM-Candidate | 0.44 ± 0.03$^b$ | 5.82 ± 0.78$^b$ | 50.87 ± 0.75$^b$ | 40.31 ± 0.46$^b$ | 22.67 ± 0.29$^b$ |

$^{a-b}$superscripts within columns indicate significant difference at $p < 0.05$.

As shown in Table 7, the tibia strength and diameter was significantly increased in turkeys fed a diet including *Bacillus*-DFM candidate compared to turkeys fed a diet without *Bacillus*-DFM candidate. The bone composition, e.g. total ash, % calcium and % phosphorus, was significantly increased in turkeys fed a diet including *Bacillus*-DFM candidate compared to turkeys fed a diet without *Bacillus*-DFM candidate.

Experiment 5

The *Bacillus*-DFM candidate was evaluated in a barley-corn (15%)-soybean diet over a 28 day period. Group 1 (control) was provided no spores in the feed (8 replicates of 20 chickens, n=160). Group 2 was provided 1×10$^6$ spores per gram of feed of the *Bacillus*-DFM candidate (8 replicates of 20 chickens, n=160). Chickens were provided a starter diet from days 0 to 7 and a grower barley-corn (15%)-soybean diet from days 8 to 28. The body weight (BW), feed intake (FI) and feed conversion rate (FCR) of the chickens was measured weekly.

TABLE 8

Evaluation of body weight, feed intake and feed conversion ratio in broiler chickens.

| Parameters | Barley-Corn (15%) | Barley-Corn (15%) + DFM-Candidate |
|---|---|---|
| Starter (0-7 d) | | |
| BW (g) | 101.6 ± 3.65$^a$ | 103.8 ± 3.26$^a$ |
| FI (g) | 135.5 ± 6.70$^a$ | 131.4 ± 4.48$^a$ |
| FCR | 1.33 ± 0.05$^a$ | 1.27 ± 0.05$^a$ |
| Grower (8-28 d) | | |
| BW (g) | 1235.1 ± 13.01$^b$ | 1291.6 ± 14.43$^a$ |
| FI (g) | 2092.9 ± 20.82$^a$ | 2046.1 ± 23.50$^a$ |
| FCR | 1.69 ± 0.01$^a$ | 1.58 ± 0.02$^b$ |
| Overall (0-28 d) | | |
| BW (g) | 1336.7 ± 13.53$^b$ | 1395.4 ± 17.02$^a$ |
| FI (g) | 2228.4 ± 23.07$^a$ | 2147.3 ± 23.62$^a$ |
| FCR | 1.66 ± 0.01$^a$ | 1.55 ± 0.02$^b$ |

$^{a-b}$superscripts within columns indicate significant difference at $p < 0.05$.

As shown in Table 8, the overall body weight of chickens fed a diet including *Bacillus*-DFM candidate was significantly increased compared to chickens fed a diet without *Bacillus*-DFM candidate. The feed intake value of chickens fed a diet including *Bacillus*-DFM candidate was not statistically different to that of chickens fed a diet without *Bacillus*-DFM candidate. The feed conversion ratio of chickens fed a diet including *Bacillus*-DFM candidate was significantly lower than chickens fed a diet without *Bacillus*-DFM candidate.

The bone breaking strength of broiler chickens fed a barley-corn-soybean diet including either a commercial DFM Sporulin® or *Bacillus*-DFM candidate was evaluated.

TABLE 9

Evaluation of bone strength and diameter in broiler chickens.

| Diet | Tibia Strength (kg/mm$^2$) | Tibia Diameter (mm) |
|---|---|---|
| Rye-Soybean | 32.2 ± 2.06$^b$ | 6.87 ± 0.11$^a$ |
| Barley-corn-soybean + Sporulin ® | 34.3 ± 2.00$^b$ | 7.20 ± 0.25$^a$ |
| Barley-corn-soybean + DFM-Candidate | 41.9 ± 1.80$^a$ | 7.01 ± 0.15$^a$ |

$^{a-b}$superscripts within columns indicate significant difference at $p < 0.05$.

As shown in Table 9, the tibia bone strength of chickens fed a diet including *Bacillus*-DFM candidate was significantly increased compared to chickens fed a diet without *Bacillus*-DFM candidate. Tibia strength of chickens fed a commercial DFM product, Sporulin® was not significantly different to chickens fed a diet without *Bacillus*-DFM candidate. The tibia diameter was not significantly different between the three groups.

TABLE 10

Evaluation of bone compensation in broiler chickens.

| Diet | Ash (%) | Ca (%) | P (%) |
|---|---|---|---|
| Rye-Soybean | 47.0 ± 0.30$^b$ | 34.9 ± 0.11$^b$ | 16.7 ± 0.03$^{ab}$ |
| Barley-corn-soybean + Sporulin ® | 48.5 ± 0.46$^a$ | 34.8 ± 0.25$^b$ | 16.5 ± 0.16$^b$ |
| Barley-corn-soybean + DFM-Candidate | 49.3 ± 0.35$^a$ | 36.0 ± 0.20$^a$ | 17.0 ± 0.06$^a$ |

$^{a-b}$superscripts within columns indicate significant difference at $p < 0.05$.

As shown in Table 10, the bone composition, e.g. total ash and % calcium, of chickens fed a diet including *Bacillus*-DFM candidate was significantly increased compared to chickens fed a diet without *Bacillus*-DFM candidate, although % phosphorus was not increased. Further, the bone composition, e.g., % calcium, of chickens fed a commercial DFM product, Sporulin® was not significantly different to chickens fed a diet without *Bacillus*-DFM candidate, although total ash and % phosphorus were increased.

Experiment 6

The effect of inclusion of *Bacillus*-DFM candidate was evaluated in broiler chickens fed a corn-soybean starter diet and a sorghum-soybean grower diet over a 27 day period. The body weight, feed intake and feed conversion ratio in the chickens was determined (Table 11). Tibia strength and tibia diameter were also determined at day 28 of treatment (Table 12).

TABLE 11

Evaluation of body weight, feed intake and feed conversion ratio in broiler chickens.

| | Control | Sporulin ® | DFM-Candidate |
|---|---|---|---|
| | Starter (0-7) | | |
| BW (g) | 133.4 ± 2.27$^{ab}$ | 126.1 ± 3.24$^b$ | 136.1 ± 2.41$^a$ |
| Feed intake (g) | 181.3 ± 7.06$^a$ | 175.5 ± 5.43$^a$ | 189.9 ± 4.43$^a$ |
| FCR | 1.36 ± 0.04$^a$ | 1.39 ± 0.04$^a$ | 1.39 ± 0.03$^a$ |
| | Grower (8-27) | | |
| BW (g) | 1214.6 ± 15.21$^b$ | 1145.7 ± 19.84$^c$ | 1268.0 ± 22.71$^a$ |
| Feed intake (g) | 1897.6 ± 16.58$^a$ | 1830.6 ± 16.73$^a$ | 1847.8 ± 37.50$^a$ |
| FCR | 1.57 ± 0.02$^a$ | 1.60 ± 0.04$^a$ | 1.46 ± 0.03$^b$ |
| | Overall (0-27) | | |
| BW (g) | 1348.0 ± 15.18$^b$ | 1271.8 ± 21.02$^c$ | 1404.2 ± 25.49$^a$ |
| Feed intake (g) | 2082.4 ± 18.42$^a$ | 2008.0 ± 19.62$^b$ | 2039.2 ± 44.02$^a$ |
| FCR | 1.55 ± 0.02$^a$ | 1.58 ± 0.04$^a$ | 1.45 ± 0.03$^b$ |

$^{a-b}$Superscripts within columns indicate significant difference at P < 0.05.

As shown in Table 11, the overall body weight of chickens fed a diet including *Bacillus*-DFM candidate was significantly increased compared to chickens fed a diet without *Bacillus*-DFM candidate. The feed intake value of chickens fed a diet including *Bacillus*-DFM candidate was not statistically different to that of chickens fed a diet without *Bacillus*-DFM candidate. The feed conversion ratio of chickens fed a diet including *Bacillus*-DFM candidate was significantly lower than chickens fed a diet without *Bacillus*-DFM candidate.

TABLE 12

Evaluation of tibia strength and diameter in broiler chickens.

| Treatment | Tibia strength (kg/mm$^2$) | Tibia diameter (mm) |
|---|---|---|
| Control | 35.77 ± 2.10$^b$ | 6.57 ± 0.12$^a$ |
| DFM - Sporulin ® | 34.46 ± 2.38$^b$ | 6.59 ± 0.11$^a$ |
| DFM - Candidate | 43.59 ± 2.07$^a$ | 6.88 ± 0.17$^a$ |

$^{a-b}$Superscripts within columns indicate significant difference at P < 0.05.

As shown in Table 12, tibia strength was significantly increased in chickens fed a sorghum-soybean grower diet with *Bacillus*-DFM candidate compared to chickens provided commercial Sporulin® or feed with no DFM. The tibia diameters were not statistically different between the three groups.

Figure 3A:
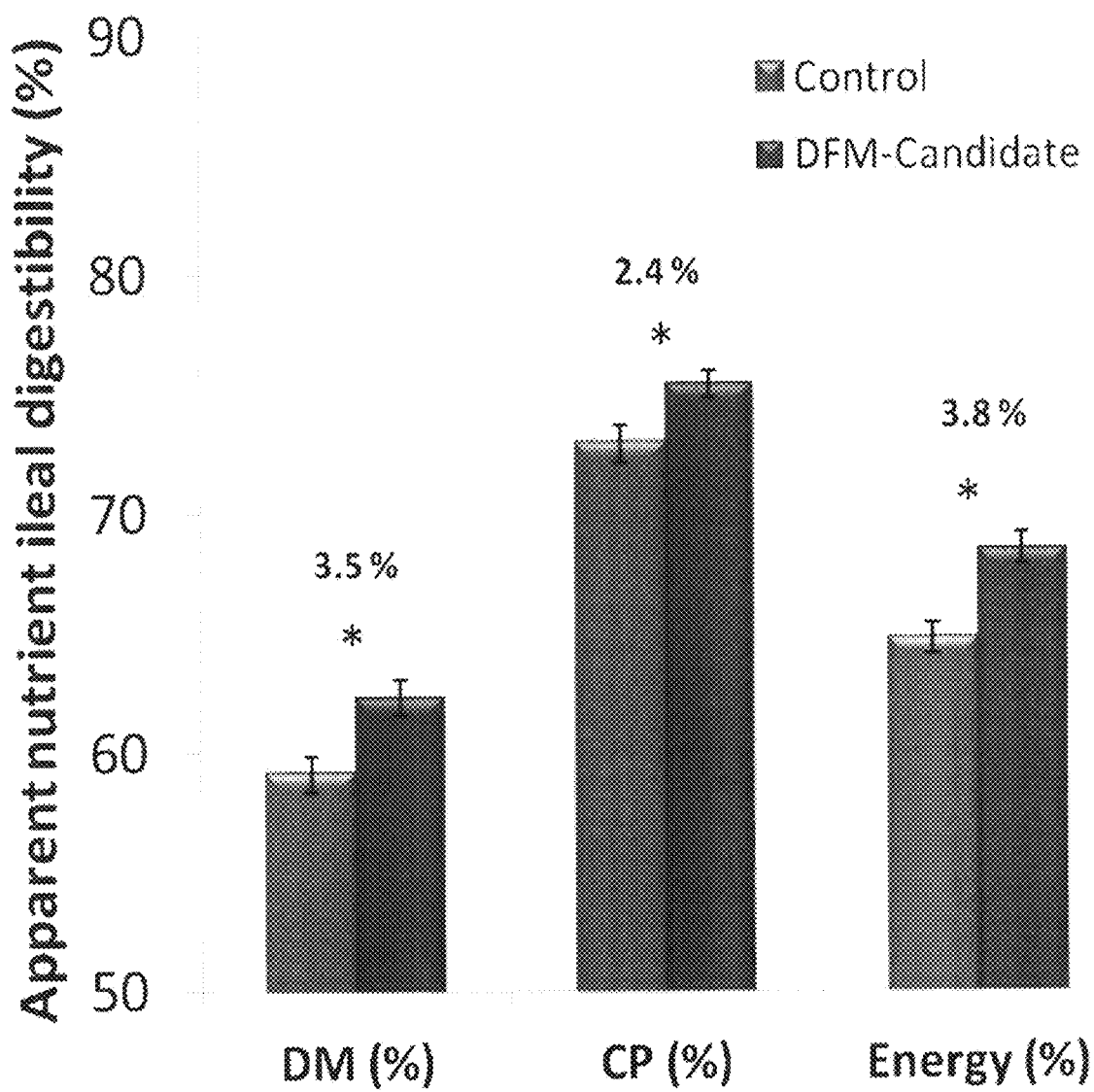
FIGS. 3A and 3B illustrate that the *Bacillus*-DFM candidate significantly improves apparent ileal nutrient digestibility for dry matter (DM), crude protein (CP), and energy (Energy) over the control group by 3.5%, 2.4%, and 3.8% respectively. Additionally
Figure 3B:
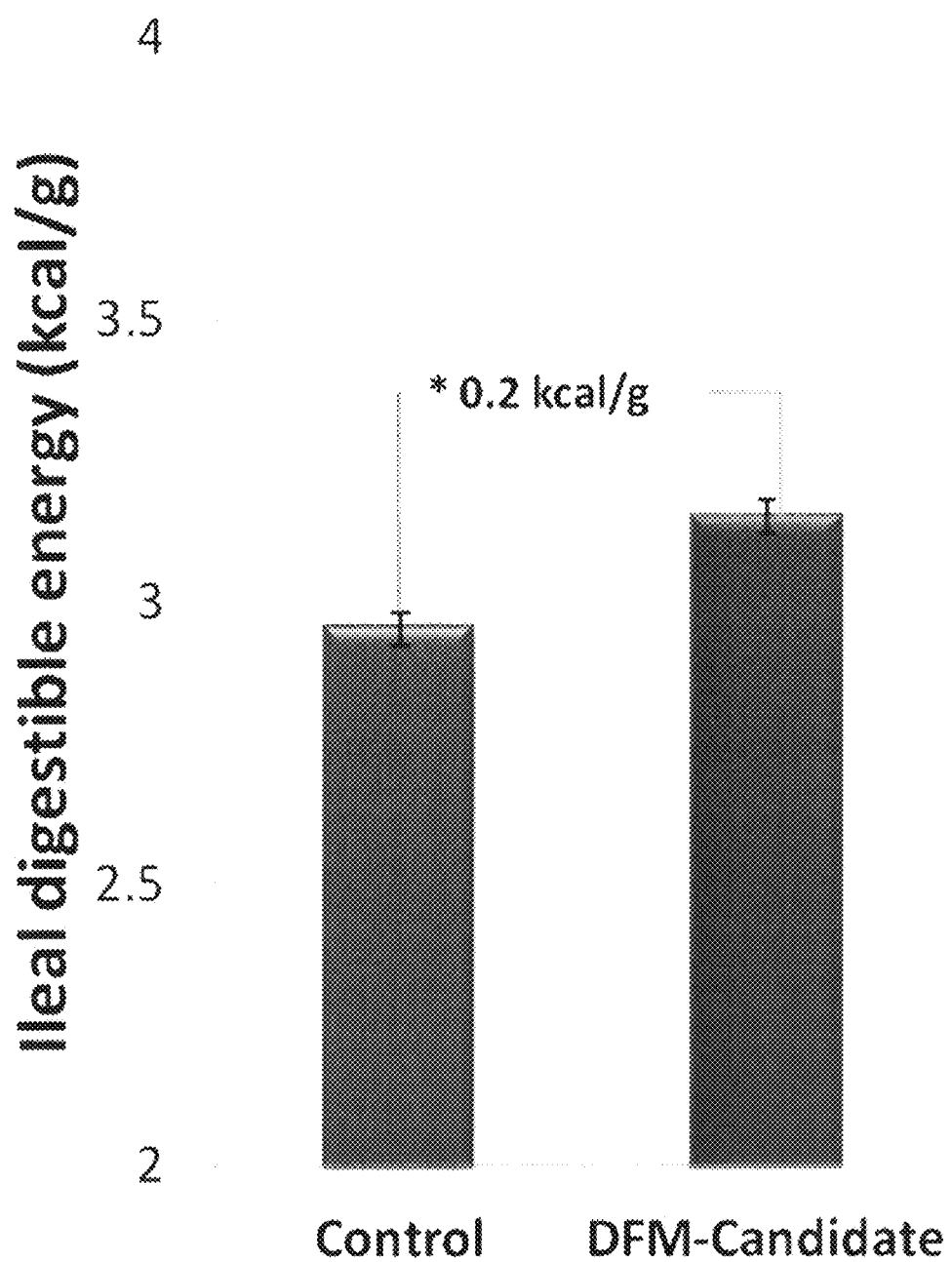

As shown in FIG. 3A, the *Bacillus*-DFM candidate significantly improved apparent ileal nutrient digestibility for (DM), crude protein (CP), and energy (Energy) over the control group by 3.5%, 2.4%, and 3.8% respectively. Additionally FIG. 3B shows that energy uptake was improved by 0.2 kcal/gram, an increase of 6.5%.

Experiment 7

The effect of inclusion of *Bacillus*-DFM candidate or Sporulin® was evaluated in broiler chickens fed a corn-DDGS (8%)-soybean grower diet over a 28 day period. *Bacillus*-DFM candidate or Sporulin® was provided at 1×10$^6$ spores per gram of feed to 8 replicates of 20 chickens per treatment (n=160 per group). The body weight, feed intake and feed conversion ratio of the chickens was determined in Experiment 7A (Table 13) and Experiment 7B (Table 14).

TABLE 13

Experiment 7A: Evaluation of body weight, feed intake and feed conversion rate in chickens.

| Parameters | Corn (no DDGS) | Corn (no DDGS) + Sporulin ® | Corn (no DDGS) + DFM-Candidate |
|---|---|---|---|
| | Starter (0-7 d) | | |
| BW (g) | 150.6 ± 3.21$^a$ | 149.3 ± 1.18$^a$ | 148.8 ± 1.15$^a$ |
| FI (g) | 177.0 ± 6.39$^a$ | 172.3 ± 5.40$^a$ | 175.1 ± 7.31$^a$ |
| FCR | 1.17 ± 0.02$^a$ | 1.15 ± 0.03$^a$ | 1.18 ± 0.04$^a$ |
| Grower (8-28 d) | Corn-DDGS (8%) | Corn-DDGS (8%) + Sporulin ® | Corn-DDGS (8%) + DFM-Candidate |
| BW (g) | 1286.4 ± 13.38$^b$ | 1297.0 ± 13.71$^{ab}$ | 1335.3 ± 14.09$^a$ |
| FI (g) | 2081.8 ± 19.75$^a$ | 2064.1 ± 23.35$^a$ | 2052.3 ± 20.84$^a$ |
| FCR | 1.62 ± 0.01$^a$ | 1.59 ± 0.02$^a$ | 1.53 ± 0.01$^b$ |
| | Overall (0-28 d) | | |
| BW (g) | 1437.0 ± 14.48$^b$ | 1446.3 ± 13.54$^{ab}$ | 1484.0 ± 14.51$^a$ |
| FI (g) | 2212.6 ± 19.92$^a$ | 2193.4 ± 23.01$^a$ | 2182.6 ± 19.58$^a$ |
| FCR | 1.54 ± 0.01$^a$ | 1.52 ± 0.01$^a$ | 1.47 ± 0.01$^b$ |

$^{a-b}$Superscripts within columns indicate significant difference at P < 0.05.

TABLE 14

Experiment 7B: Evaluation of body weight, feed intake and feed conversion rate in chickens.

| Parameters | Corn (no DDGS) | Corn (no DDGS) + Sporulin ® | Corn (no DDGS) + DFM-Candidate |
|---|---|---|---|
| | Starter (0-7 d) | | |
| BW (g) | 115.3 ± 1.74$^a$ | 115.2 ± 1.08$^a$ | 116.2 ± 1.53$^a$ |
| FI (g) | 130.8 ± 3.24$^a$ | 129.1 ± 2.42$^a$ | 130.5 ± 2.33$^a$ |
| FCR | 1.13 ± 0.01$^a$ | 1.12 ± 0.02$^a$ | 1.12 ± 0.02$^a$ |
| Grower (8-28 d) | Corn-DDGS (8%) | Corn-DDGS (8%) + Sporulin ® | Corn-DDGS (8%) + DFM-Candidate |
| BW (g) | 1294.0 ± 8.74$^b$ | 1324.0 ± 8.15$^a$ | 1328.0 ± 12.13$^a$ |
| FI (g) | 1879.0 ± 10.21$^a$ | 1819.0 ± 14.26$^b$ | 1838.0 ± 13.29$^b$ |
| FCR | 1.45 ± 0.01$^a$ | 1.37 ± 0.01$^b$ | 1.38 ± 0.01$^b$ |
| | Overall (0-28 d) | | |
| BW (g) | 1409.0 ± 7.93$^b$ | 1439.0 ± 7.85$^a$ | 1444.0 ± 12.56$^a$ |
| FI (g) | 2010.0 ± 9.66$^a$ | 1948.6 ± 14.54$^b$ | 1966.6 ± 13.26$^b$ |
| FCR | 1.43 ± 0.01$^a$ | 1.35 ± 0.01$^b$ | 1.36 ± 0.01$^b$ |

$^{a-b}$Superscripts within columns indicate significant difference at P < 0.05.

As shown in Tables 13 and 14, body weight was significantly increased in chickens fed a diet including *Bacillus*-DFM candidate and a diet including Sporulin® compared to chickens fed a diet without a DFM (Experiments 7A and 7B). There was no significant difference in feed intake between the 3 groups in Experiment 7A (Table 13). In Experiment 7B, feed intake was significantly decreased in chickens fed a diet including either *Bacillus*-DFM candidate or Sporulin® compared to chickens fed a diet without a DFM (Table 14). The feed conversion ratio was significantly decreased in chickens fed a diet including *Bacillus*-DFM candidate compared to chickens fed a diet without a DFM or a diet including Sporulin® (Experiments 7A and 7B).

The tibias from 8 chickens per treatment group were collected to evaluate bone strength and bone composition, e.g. percent calcium and percent phosphorus, from Experiment 7B.

TABLE 15

Experiment 7C: Evaluation of bone strength and bone composition in chickens.

| Diet | Corn-DDGS (8%) | Corn-DDGS (8%) + Sporulin ® | Corn-DDGS (8%) + DFM-Candidate |
|---|---|---|---|
| Load at Yield (kg) | 35.85 ± 1.47[b] | 35.38 ± 2.18[b] | 42.88 ± 2.75[a] |
| Tibia diameter (mm) | 6.84 ± 0.21[a] | 6.85 ± 0.19[a] | 7.14 ± 0.31[a] |
| Breaking strength (kg/mm$^2$) | 5.26 ± 0.19[b] | 5.16 ± 0.29[b] | 5.99 ± 0.22[a] |
| Ca (%) | 35.24 ± 0.10[b] | 36.36 ± 0.35[b] | 39.26 ± 0.24[a] |
| P (%) | 16.60 ± 0.30[b] | 17.75 ± 0.25[b] | 20.83 ± 0.66[a] |

[a-b]Superscripts within columns indicate significant difference at $P < 0.05$.

As shown in Table 15, the load at yield, and breaking strength were significantly increased in chickens fed a diet including *Bacillus*-DFM candidate compared to chickens fed a diet including Sporulin® or a diet without DFM. The tibia diameter was not significantly different between the three groups. The percentage of calcium and phosphorus within the tibia was significantly increased in chickens fed a diet including *Bacillus*-DFM candidate compared to chickens fed a diet including Sporulin® or a diet without DFM.

Inclusion of a *Bacillus*-DFM candidate increased body weight, bone strength and bone composition in chickens fed diets having high non-starch polysaccharides (NSP).

It is believed that the disclosure set forth above encompasses at least one distinct invention with independent utility. While the invention has been disclosed in the exemplary forms, the specific embodiments thereof as disclosed and illustrated herein are not to be considered in a limiting sense as numerous variations are possible. Equivalent changes, modifications and variations of various embodiments, materials, compositions and methods may be made within the scope of the present invention, with substantially similar results. The subject matter of the inventions includes all novel and non-obvious combinations and subcombinations of the various elements, features, functions and/or properties disclosed herein.

Benefits, other advantages, and solutions to problems have been described herein with regard to specific embodiments. However, the benefits, advantages, solutions to problems, and any element or combination of elements that may cause any benefit, advantage, or solution to occur or become more pronounced are not to be construed as critical, required, or essential features or elements of any or all the claims of the invention. Many changes and modifications within the scope of the instant invention includes all such modifications. Corresponding structures, materials, acts, and equivalents of all elements in the claims below are intended to include any structure, material, or acts performing the functions in combination with other claim elements as specifically claimed. The scope of the invention should be determined by the appended claims and their legal equivalents, rather than by the examples given above.

Experiment 8

TABLE 16

Relative Enzyme Activity (REA) in mm

| Number | Identification | Cellulase 48 h | Protease 24 h | Lipase 24 h | Xylanase 24 h | Phytase 120 h | Average Score |
|---|---|---|---|---|---|---|---|
| 1 | NP122 (NRRL B-50910) | 1.78 | 2.79 | 2.78 | 3.47 | 1.34 | 2.33 |
| 2 | JD17 | 1.74 | 2.72 | 2.54 | 2.58 | 1.69 | 2.25 |
| 3 | AM1109A | 1.00 | 1.64 | 2.36 | 3.03 | 1.35 | 1.88 |
| 4 | AM1109B | 1.40 | 2.41 | 2.60 | 3.13 | 1.37 | 2.18 |
| 5 | NP124 | ND | ND | ND | ND | ND | ND |
| 6 | AM0902 | 1.67 | 1.95 | 3.15 | 1.00 | 1.56 | 1.86 |
| 7 | B2 (NRRL B-50908) | 1.25 | 2.76 | 2.47 | 2.73 | 1.61 | 2.17 |
| 8 | RW41 | 1.15 | 1.19 | 2.35 | 1.13 | 1.29 | 1.62 |
| 9 | B.L | ND | ND | ND | ND | ND | ND |
| 10 | AM0904 | 1.00 | 2.35 | 2.31 | 1.00 | 1.17 | 1.57 |
| 11 | AM1010 | 1.58 | 2.40 | 2.49 | 1.43 | 1.52 | 1.88 |
| 12 | AM1101 | 1.68 | 2.91 | 2.36 | 4.15 | 1.34 | 2.49 |
| 13 | AM1012 | 1.50 | 2.43 | 2.35 | 2.59 | 1.34 | 2.04 |
| 14 | AM1013 | 2.13 | 2.67 | 2.78 | 3.25 | 1.63 | 2.49 |
| 15 | AM0923 | 1.78 | 2.98 | 2.24 | 2.87 | 1.50 | 2.27 |
| 16 | 19/49 | ND | ND | ND | ND | ND | ND |
| 17 | AM0908 | 1.67 | 1.93 | 2.14 | 1.07 | 1.51 | 1.67 |
| 18 | AM0905 | 1.22 | 2.40 | 2.73 | 2.79 | 1.55 | 2.14 |
| 19 | AM0939 | 1.72 | 2.95 | 2.19 | 2.29 | 1.35 | 2.10 |
| 20 | AM0940 | 1.24 | 2.09 | 2.25 | 3.41 | 1.42 | 2.14 |
| 21 | AM 1002 | 1.15 | 2.36 | 2.90 | 2.35 | 1.39 | 2.03 |
| 22 | AM0933 | 1.43 | 2.16 | 2.16 | 3.67 | 1.48 | 2.18 |
| 23 | AM0934 | 1.29 | 3.06 | 2.20 | 2.88 | 1.27 | 2.14 |
| 24 | AM0938 | 2.12 | 2.62 | 2.41 | 4.23 | 1.37 | 2.55 |
| 25 | AM0941 | 1.61 | 1.95 | 2.92 | 2.53 | 2.07 | 2.22 |
| 26 | NP117B | 1.22 | 2.95 | 2.11 | 2.47 | 1.32 | 2.01 |
| 27 | NP121 | 1.00 | 2.15 | 2.00 | 1.28 | 1.47 | 1.58 |
| 28 | MM65 | 1.21 | 1.00 | 2.78 | 4.19 | 2.67 | 2.37 |
| 29 | NP001 | ND | ND | ND | ND | ND | ND |
| 30 | NP002 | ND | ND | ND | ND | ND | ND |
| 31 | NP126 | 1.67 | 2.46 | 2.44 | 3.56 | 1.17 | 2.26 |

ND: Not determined.

In this experiment 26 of the 31 *Bacillus* isolates previously evaluated in experiment 1 were evaluated to confirm their ability to produce different enzyme activities (e.g., the production of protease, cellulase, lipase, xylanase, and phytase).

The bacterial candidates were incubated in tryptic soy broth (TSB; BD Difco Tryptic Soy Broth) media overnight at 37° C. under shaking condition. The bacterial candidates were washed 3 times in saline by centrifugation at 3000 g for 15 minutes at 4° C.

Bacterial candidates were screened for the production of cellulase, protease, xylanase, lipase, and phytase enzyme activity. Bacterial candidates were plated on agar plates containing Spirit Blue Agar (incubated for 24 hours; lipase), carboxymethyl cellulose (CMC) Congo red agar (incubated for 48 hours; cellulase), milk agar (incubated for 48 hours; protease), Na-phytate agar (incubated for 48 hours; phytase), and beechwood xylan agar (incubated for 48 hours; xylanase). Bacterial growth and zone/area of clearance were determined by measuring in millimeters (mm). Relative enzyme activity (REA) was determined by using the following formula:

REA=diameter of zone of clearance with bacterial colony in mm/diameter of the bacterial colony in mm

The invention claimed is:

1. A probiotic composition for improving digestion of nutrients in an animal comprising:
    (a) at least two enzyme producing *Bacillus* isolates selected from the group consisting of:
    *Bacillus amyloliquefaciens* JD17 (NRRL Deposit B-67142),
    *Bacillus licheniformis* AM11002 (NRRL Deposit B-67143),
    *Bacillus amyloliquefaciens* AM10938 (NRRL Deposit B-67144),
    *Bacillus amyloliquefaciens* AM10933 (NRRL Deposit B-67277),
    *Bacillus amyloliquefaciens* AM11109B (NRRL Deposit B-67146),
    *Bacillus amyloliquefaciens* AM11101 (NRRL Deposit B-67147),
    *Bacillus amyloliquefaciens* AM10939 (NRRL Deposit B-67148),
    *Bacillus amyloliquefaciens* AM10934 (NRRL Deposit B-67149),
    *Bacillus amyloliquefaciens* AM10940 (NRRL Deposit B-67278), and
    any combination thereof, and
    (b) an agriculturally acceptable excipient.

2. The probiotic composition of claim 1, wherein the at least two enzyme producing *Bacillus* isolates produce phytase, protease, lipase, cellulase, and xylanase.

3. The probiotic composition of claim 1, wherein the at least two enzyme producing *Bacillus* isolates form a biofilm.

4. The probiotic composition of claim 1, wherein the at least two enzyme producing *Bacillus* isolates are spore forming *Bacillus*.

5. The probiotic composition of claim 4, wherein the spore forming *Bacillus* produces at least about $1 \times 10^4$ to about $1 \times 10^{11}$ spores per gram of bacteria.

6. The probiotic composition of claim 1, wherein the probiotic composition is provided in an animal feed.

7. The probiotic composition of claim 6, wherein the probiotic composition is included in the animal feed during pelleting.

8. The probiotic composition of claim 6, wherein the animal feed is bird feed.

9. The probiotic composition of claim 8, wherein the bird feed comprises corn, soybean, rye, barley, wheat, oats, sorghum, distiller's dried grains with solubles, or any combination thereof.

10. The probiotic composition of claim 6, wherein the probiotic composition is included in the animal feed at $1 \times 10^4$ to $1 \times 10^{10}$ colony forming units per gram of feed.

11. The probiotic composition of claim 1, wherein the improved digestion of nutrients corresponds to an increase in one or more parameters or indications.

12. The probiotic composition of claim 11, wherein the one or more parameters or indications is body weight, bone strength and/or bone composition.

13. The probiotic composition of claim 12, wherein the bone composition is measured as total ash, calcium content and phosphorus content.

14. A method for improving digestion of nutrients in an animal comprising providing a probiotic composition comprising at least two enzyme producing *Bacillus* bacterial isolates selected from the group consisting of
    *Bacillus amyloliquefaciens* JD17 (NRRL Deposit B-67142),
    *Bacillus licheniformis* AM11002 (NRRL Deposit B-67143),
    *Bacillus amyloliquefaciens* AM10938 (NRRL Deposit B-67144),
    *Bacillus amyloliquefaciens* AM10933 (NRRL Deposit B-67277),
    *Bacillus amyloliquefaciens* AM11109B (NRRL Deposit B-67146),
    *Bacillus amyloliquefaciens* AM11101 (NRRL Deposit B-67147),
    *Bacillus amyloliquefaciens* AM10939 (NRRL Deposit B-67148),
    *Bacillus amyloliquefaciens* AM10934 (NRRL Deposit B-67149), and
    *Bacillus amyloliquefaciens* AM10940 (NRRL Deposit B-67278), and
    any combination thereof, and
    an agriculturally acceptable excipient to the animal.

15. The method of claim 14, wherein one or more parameters or indications are improved.

16. The method of claim 15, wherein the one or more parameters or indications is body weight, feed intake, feed conversion ratio, bone strength, bone composition, viscosity, or bacterial translocation.

17. The method of claim 14, wherein the probiotic composition is provided in an animal feed.

* * * * *